US012697372B2

(12) United States Patent  (10) Patent No.: US 12,697,372 B2
Heiser et al.  (45) Date of Patent: Aug. 4, 2026

(54) COMPOSITION COMPRISING HP-HMG FOR USE IN TREATING INFERTILITY

(71) Applicant: FERRING B.V., Hoofddorp (NL)

(72) Inventors: Patrick Heiser, Parsippany, NJ (US); Eric Foster, Parsippany, NJ (US)

(73) Assignee: Ferring B.V., Hoofddorp (NL)

( * ) Notice: Subject to any disclaimer, the term of this patent is extended or adjusted under 35 U.S.C. 154(b) by 908 days.

(21) Appl. No.: 17/928,176

(22) PCT Filed: May 28, 2021

(86) PCT No.: PCT/EP2021/064376
§ 371 (c)(1),
(2) Date: Nov. 28, 2022

(87) PCT Pub. No.: WO2021/239961
PCT Pub. Date: Dec. 2, 2021

(65) Prior Publication Data
US 2023/0210955 A1  Jul. 6, 2023

Related U.S. Application Data

(60) Provisional application No. 63/032,430, filed on May 29, 2020.

(30) Foreign Application Priority Data

Jun. 29, 2020  (EP) .................................... 20182800

(51) Int. Cl.
| | | |
|---|---|---|
| *A61K 38/24* | (2006.01) | |
| *A61B 17/435* | (2006.01) | |
| *A61P 15/08* | (2006.01) | |

(52) U.S. Cl.
CPC ............ *A61K 38/24* (2013.01); *A61B 17/435* (2013.01); *A61P 15/08* (2018.01)

(58) Field of Classification Search
None
See application file for complete search history.

(56) References Cited

U.S. PATENT DOCUMENTS

| | | | |
|---|---|---|---|
| 10,413,592 | B2 | 9/2019 | Arce et al. |
| 11,351,228 | B2 | 6/2022 | Arce et al. |
| 2005/0020489 | A1 | 1/2005 | Menezo |
| 2021/0093697 | A1 | 4/2021 | Arce et al. |
| 2023/0248807 | A1 | 8/2023 | Heiser |
| 2025/0114434 | A1 | 4/2025 | Cottingham |

FOREIGN PATENT DOCUMENTS

WO  WO-2016135221 A1 *  9/2016  .............. A61P 15/08

OTHER PUBLICATIONS

Andersen et al., "Clinical outcome following stimulation with highly purified hMG or recombinant FSH in patients undergoing IVF: a randomized assessor-blind controlled trial", Human Reproduction vol. 21, No. 12 pp. 3217-3227, 2006. (Year: 2006).*
Eurasian Search Report issued in Eurasian Application No. 202492676 dated Feb. 18, 2025.
A. La Marca et al: "Anti-Mullerian hormone measurement on any day of the menstrual cycle strongly predicts ovarian response in assisted reproductive technology", Human Reproduction, vol. 22, No. 3, Dec. 7, 2006 (Dec. 7, 2006), pp. 766-771, P055285184, GB ISSN: 0268-1161, DOI: 10.1093/humrep/del421.
Angeline N Beltsos et al: "Patients' administration preferences: progesterone vaginal insert (Endometrin) compared to intramuscular progesterone for Luteal phase support", Reproductive Health, Biomed Central, London, GB, vol. 11, No. 1, Nov. 11, 2014 (Nov. 11, 2014), p. 78, XP021220668, ISSN: 1742-4755, DOI: 10.1186/1742-4755-11-78.
Arce Joan-Carles et al: "The rate of high ovarian response in women identified at risk by a high serum AMH level is influenced by the type of gonadotropin", Gynecological Endocrinology, vol. 30, No. 6, Jun. 19, 2014 (Jun. 19, 2014), pp. 444-450, XP055784562, GB ISSN: 0951-3590, DOI: 10.3109/09513590.2014.892066.
C.S. Sipe et al., Using gonadotropins with hCG activity improves controlled response in PCOS patients undergoing IVF compared to cycles using FSH alone. Fertility and Sterility, Poster (2008).
C.S. Sipe et al., Using gonadotropins with hCG activity improves controlled response in PCOS patients undergoing IVF compared to cycles using FSH alone. Fertility and Sterility, vol. 90, Supplement, S132-S133, Abstract P-65, Sep. 2008 DOI:https://doi.org/10.1016/j.fertnstert.2008.07.198.
Examination Report received in Saudi Arabian Patent Application No. 522441887, dated Oct. 26, 2023 (with English summary).
Foreign Search Report received in Chilean Patent Application No. 202203746 dated Apr. 16, 2024.
Heiser et al., Predicted high-responder women diagnosed with oligoovulation may benefit from stimulation with highly purified human menopausal gonadotrophin (HP-hMG), Eur. Soc. Hum. Reprod. Embryol. (ESHRE), Virtual Meeting Jul. 5-8, 2020, Abstract O-012.
Heiser et al., Predicted high-responder women diagnosed with oligoovulation may benefit from stimulation with highly purified human menopausal gonadotrophin (HP-hMG), Eur. Soc. Hum. Reprod. Embryol. (ESHRE), Virtual Meeting Jul. 5-8, 2020, Abstract O-012 (on-line version published May 2020).
International Preliminary Report on Patentability dated Dec. 13, 2022 received in PCT/US2020/039745.
International Search Report and Written Opinion received in PCT/US2020/039745 dated Mar. 29, 2021.
Kemmann E et al: "Induction of Ovulation With Menotropins in Women With Poly Cystic Ovary Syndrome", Database accession No. PREV198273027247; & American Journal of Obstetrics and Gynecology, vol. 141, No. 1, 1981, pp. 58-64, ISSN: 0002-9378.
La Marca et al., IVF/ICSI Patients Predicted to be High Responders by Their AMH Level May Benefit From HP-HMG Treatment. Fertility and Sterility O-169 (2012).

(Continued)

*Primary Examiner* — Yi-Shan Yang
(74) *Attorney, Agent, or Firm* — Foley & Lardner LLP

(57) ABSTRACT

The present invention relates to improved assisted reproductive technology for women predicted to have a high ovarian response to controlled ovarian stimulation that comprise targeting a threshold serum hCG level by the final day of stimulation.

19 Claims, No Drawings

(56) References Cited

OTHER PUBLICATIONS

Menopur Prescribing Information (May 2018).

N.A. Malini et al. "Evaluation of different ranges of LH:FSH ratios in polycystic ovarian syndrome (PCOS)—Clinical based case control study" General and Comparative Endocrinology 260; Accepted Dec. 16, 2017; 2018 Elsevier Inc.

Patrick Heiser et al. "Predicted high responder women diagnosed with oligoovulation may benefit from stimulation with highly purified human menopausal gonadotrophin (HP-hMG)" Abstract; European Society of Human Reproduction and Embryology; published on May 12, 2020.

Patrick Heiser et al.; Predicted high responder women diagnosed with oligoovulation79094 3 may benefit from stimulation with highly purified human menopausal gonadotrophin (HP-hMG);36th Annual Congress of the European Society for Human Reproduction and Embryology of Jul. 2020, published online dated May 12, 2020 (sildes and summary).

Repronexo (Menotropins for Injection, USP) (Ferring Pharmaceuticals) (Aug. 18, 1999).

Richard Buyalos et al. "Polycystic ovary syndrome: pathophysiology and outcome with in vitro fertilization" Fertility and Sterility (1996) vol. 65 (1) p. 1-10.

S. Ziebe et al: "Influence of ovarian stimulation with HP-hMG or recombinant FSH on embryo quality parameters in patients undergoing IVF", Human Reproduction, vol. 22, No. 9, Jun. 28, 2007 (Jun. 28, 2007), pp. 2404-2413, XP055208240, ISSN: 0268-1161, DOI: 10.1093/humrep/dem221.

Vuong Lan N et al: "Live births after oocyte in vitro maturation with a prematuration step in women with polycystic ovary syndrome", Journal of Assisted Reproduction and Genetics, Plenum Publishing, US, vol. 37, No. 2, Jan. 4, 2020 (Jan. 4, 2020), pp. 347-357, XP037050746.

Wallach Edward E et al: "Polycystic ovary syndrome: pathophysiology and outcome with in vitro fertilization", Fertility and Sterility, vol. 65, No. 1 , pp. 1-10, XP029524561.

Amer, S.A. et al. 'The influence of circulating anti-Mullerian hormone on ovarian responsiveness to ovulation induction with gonadotrophins in women with polycystic ovarian syndrome: a pilot study' Reproductive Biology and Endocrinology, vol. 11, No. 1, 2013, pp. 115-123.

Arce, J-C et al. Antimullerianormone in gonadotropin releasing-hormone antagonist cycles: prediction of ovarian response and cumulative treatment outcome in good-prognosis patients, Fertility and Sterility, vol. 99, No. 6, 2013, pp. 1644-1653.

Hilwah, N. et al."Impact of serum human chorionic gonadotropin and luteinizing hormone receptor expres-sion to oocyte maturation rate: A study of controlled ovarian stimulation", vol. 13, No. 1, 2020, pp. 46-50.

Technical Examination Report issued by the Danish Patent and Trademark Office dated Jan. 29, 2021; reference No. PA 2020 00877.

Witz, et al. "Randomized, assessor-blinded trial comparing highly purified human menotropin and recombinant follicle-stimulating hormone in high responders undergoing intracytoplasmic sperm injection", Fertility and Sterility, 114(2): 321-30 (Aug. 2020) (published on line May 13, 2020).

Zhang, L. et al. "Correlation of follicular fluid human chorionic gonadotrophin level with oocyte maturity and early embryonic development" Nan fang yi ke da xue xue bao (=Journal of Southern Medical University), vol. 34, No. 2, 2014, pp. 260-264.

Foreign Office Action dated Jul. 15, 2025, issued in Japanese Application No. 2022-573348.

Restriction Requirement dated Jul. 28, 2025, in U.S. Appl. No. 18/012,753.

Tal et al., "Characterization of women with elevated antimüllerian hormone levels (AMH): correlation of AMH with polycystic ovarian syndrome phenotypes and assisted reproductive technology outcomes," Am. J. Obstetrics & Gynecol. Jul. 2014; 211:59.e1-8.

A. La Marca et al: "Anti-Mullerian hormone measurement on any day of the menstrual cycle strongly predicts ovarian response in assisted reproductive technology", Human Reprod., vol. 22, No. 3, pp. 766-771, 2007 (published on-line Oct. 27, 2006).

Arce and Smitz, "Exogenous hCG activity, but not endogenous LH activity, is positively associated with live birth rates in anovulatory infertility Human Fertility" 14(3): 192-99 (2011).

Arce and Smitz, "Live-birth rates after HP-hMG stimulation in the long GnRH agonist protocol: association with mid-follicular hCG and progesterone concentrations, but not with LH concentrations" Gynecol. Endocrinol. 29(1): 46-50 (2013).

Devroey et al., "A randomized assessor-blind trial comparing highly purified hMG and recombinant FSH in a GnRH antagonist cycle with compulsory single-blastocyst transfer" Fertility and Sterility 97: 561-71 (2012).

Esteves Sandro C et al: "A comparison of menotropin, highly-purified menotropin and follitropin alfa in cycles of intracytoplasmic sperm injection", Reprod. Biol. Endocrinol., vol. 7, No. 1, Oct. 14, 2009 (Oct. 14, 2009), p. 111.

Extended European Search Report issued in EP Application No. 20182800.1 dated Nov. 11, 2020.

Foutouh et al., "Clinical outcome following stimulation with HMG versus highly purifi ed HMG in patients undergoing ICSI" Reproductive BioMed. Online, 14(2): 145-47 (2007).

La Marca et al.,"IVF/ICSI Patients Predicted to be High Responders by Their AMH Level May Benefit From HP-HMG Treatment" Fertility and Sterility; O-169 Oct. 23, 2012.

Prescribing Information for Novarel (Chorionic Gonadotropin for Injection, USP) (2018).

Prescribing Information MENOPUR (menotropins for injection) for subcutaneous use. Initial U.S. Approval: 1975; May 2018-Mar. 2019.

Rubio et al., Prospective cohort study in high responder oocyte donors using two hormonal stimulation protocols: impact on embryo aneuploidy and development Human Reproduction 25(9): 2290-97 (2010).

Taronger Roser et al: "Ovarian stimulation with corifollitropin alfa followed by hp-hMG compared to hp-hMG in patients at risk of poor ovarian response undergoing ICSI: A randomized controlled trial", Eur. J. Ob. & Gyn. Reprod. Biol., vol. 231, Oct. 13, 2018 (Oct. 13, 2018), pp. 192-197.

Wolfenson et al., "Batch-to-batch consistency of human-derived gonadotrophin preparations compared with recombinant preparations" Reprod. BioMed. Online, 10(4): 442-54 (2005).

Ziebe et al., "Influence of ovarian stimulation with HP-hMG or recombinant FSH on embryo quality parameters in patients undergoing IVF," Human Reproduction 22(9) 2404-13 (2007).

Patent Examination Report issued in NZ Application No. 795074 dated Sep. 24, 2025.

* cited by examiner

COMPOSITION COMPRISING HP-HMG FOR USE IN TREATING INFERTILITY

CROSS-REFERENCE TO RELATED APPLICATIONS

The present application is the U.S. National Stage of International Application No. PCT/EP2021/064376, filed May 28, 2021, which claims priority to U.S. Provisional Application 63/032,430, filed May 29, 2020, and to European Patent Application No. 20182800.1, filed Jun. 29, 2020.

FIELD OF INVENTION

The invention described herein relates to assisted reproductive technology. In particular, described herein are compositions and methods for treating infertility, including controlled ovarian stimulation methods that may be particularly useful for women who are predicted to have a high ovarian response to controlled ovarian stimulation.

BACKGROUND OF THE INVENTION

Assisted reproductive technology (ART) procedures generally involve stimulating egg development and maturation, harvesting eggs from a woman's ovaries, combining them with sperm in vitro, and transferring them to a woman's uterus (the donor or another woman). Success of ART is hampered by maternal and perinatal risks associated with the stimulation of egg development and maturation, such as ovarian hyperstimulation syndrome (OHSS) and ectopic pregnancy. Other concerns that arise in ART are the production of quality embryos and euploid blastocysts to support ongoing pregnancy rates and live birth rates.

Gonadotropins, such as menotropin (e.g., human menopausal gonadotropin, or hMG), follicle-stimulating hormone (FSH) and luteinizing hormone (LH), have been used for controlled ovarian stimulation (COS), and highly purified menotropin (HP-hMG) and recombinant human FSH (rFSH) have been used more recently. HP-hMG provides FSH and exogenous LH activity mainly in the form of human chorionic gonadotrophin (hCG). The efficacy of ovarian stimulation protocols may be enhanced using long gonadotropin hormone releasing hormone (GnRH) agonists or GnRH antagonists for cycle control. See, e.g., Devroey et al., *Fertility and Sterility* 97: 561-71 (2012). Ziebe et al., *Human Reproduction* 22(9) 2404-13 (2007), reported that the use of HP-hMG versus rFSH could impact the morphology of embryos, and observed improved implantation, ongoing pregnancy and live birth rates among the top-quality embryos (based on visual assessment) derived from stimulation with HP-hMG compared with Chinese hamster ovary cell (CHO cell)-derived rFSH (GONAL-F).

Because patient responses to ovarian stimulation vary widely, treatments often are individualized. For example, individualization may be based on predicted ovarian response to gonadotropin stimulation, which forecasts poor, normal or high response. High ovarian responders usually are defined as women who produce high numbers of developing follicles following a standard protocol of controlled ovarian stimulation (COS). Although these patients are generally considered good candidates for ART, high ovarian response may be associated with lower implantation rates and higher miscarriage rates, and thus a decreased chance of successful outcome as compared with a normal ovarian response. These high responders also are at greater risk for OHSS and the complications associated therewith.

Efforts to develop improved ART methods for predicted high responders have involved exploring milder stimulation protocols. For example, Rubio et al., *Human Reproduction* 25(9): 2290-97 (2010), reported that decreasing the gonadotropin dose administered to high responders could improve fertilization rates and embryo quality, although the lower doses resulted in fewer oocytes. Other efforts have considered whether the specific gonadotropin used impacts the results. For example, La Marca et al., *Fertility and Sterility* 0-169 (2012), reported that among predicted high responders (subjects having an AMH≥5.2 ng/ml) the group stimulated with CHO cell-derived rFSH (GONAL-F) had significantly more oocytes retrieved, but a significantly lower live birth rate per cycle as compared to the group stimulated with HP-hMG (20% vs. 33% in the MERIT "long agonist" clinical trial; 23% vs. 34% in the MEGASET "antagonist" trial).

There remains a need for improved assisted reproductive technology methods, particularly for women predicted to have a high response to controlled ovarian stimulation.

SUMMARY OF THE INVENTION

The compositions and methods described herein stem from the surprising and unexpected discovery that, in HP-hMG treated subjects predicted to be high-responders, serum hCG on the last day of stimulation is a significant predictor of the probability of live birth, with higher serum hCG being correlated with a higher chance of live birth. In other words, the compositions and methods described herein stem from the surprising and unexpected discovery that determining serum hCG at a mid-follicular stage of stimulation and adjusting HP-hMG dosing to achieve a target serum hCG on the last day of stimulation is associated with a higher probability of live birth.

Provided herein are methods of treating infertility by controlled ovarian stimulation in a patient predicted to have a high ovarian response to controlled ovarian stimulation, comprising selecting a patient identified as predicted to have a high ovarian response to controlled ovarian stimulation; conducting controlled ovarian stimulation by administering to the selected patient HP-hMG at a starting daily dose of 75 IU to 225 IU; at a mid-follicular stage of controlled ovarian stimulation, determining if the patient's serum level of hCG is at a target mid-follicular threshold level; and optionally, maintaining or increasing the daily dose of HP-hMG based on whether the patient's serum level of hCG is at or below the target mid-follicular threshold level. Typically, patient is not an anovulatory patient. The patient may be 21-35 years old and may have a BMI of 18-30 kg/m² at the start of treatment. The method may comprise increasing the daily dose of HP-hMG when the patient's serum level of hCG is below the target mid-follicular threshold level. The method may comprise increasing the daily dose of HP-hMG by 75 IU/day when the patient's serum level of hCG is below the target mid-follicular threshold level. The method may comprise maintaining the daily dose of HP-hMG when the patient's serum level of hCG is at the target mid-follicular threshold level. The target mid-follicular threshold level of serum hCG may be ≥1.5 mIU/mL. The mid-follicular stage of controlled ovarian stimulation may be selected from stimulation day 5, stimulation day 6, and stimulation day 7. The starting daily dose of HP-hMG may be 150 IU/day. The method may further comprise administering a gonadotropin-releasing hormone antagonist (GnRH antagonist) starting on day 6 of stimulation. The method may further comprise triggering final follicular maturation by administering human chorionic gonadotropin (hCG) or a gonadotropin-releasing hormone agonist (GnRH agonist), optionally supplemented with hCG. The method may further comprise (a) retrieving oocyte(s), fertilizing the oocyte(s), allowing the fertilized oocyte(s) to develop to the blastocyst stage, optionally assessing the quality/morphology of the blastocyst(s), and implanting a fresh blastocyst (optionally selected based on, e.g., visual assessment of quality/morphology) in a uterus; (b) retrieving oocyte(s), fertilizing the oocyte(s), allowing the fertilized oocyte(s) to develop to the blastocyst stage, optionally assessing chromosomal quality of the blastocyst(s), freezing one or more or all blastocyst(s), and implanting a thawed-frozen blastocyst (e.g., a euploid blastocyst selected based on chromosomal assessment) in a uterus; (c) retrieving oocyte(s), freezing unfertilized oocytes(s), subsequently thawing one or more oocyte(s), fertilizing one or more or all thawed oocyte(s), allowing fertilized oocyte(s) to develop to the blastocyst stage, optionally assessing the quality/morphology of the blastocyst(s), and implanting a blastocyst (optionally selected based on, e.g., visual assessment of quality/morphology) in a uterus; or (d) retrieving oocyte(s), freezing unfertilized oocytes(s), subsequently thawing one or more frozen oocytes, fertilizing one or more or all thawed oocyte(s), allowing fertilized oocyte(s) to develop to the blastocyst stage, optionally assessing chromosomal quality of the blastocyst(s), freezing one or more or all blastocyst(s), and implanting a thawed-frozen blastocyst (e.g., a euploid blastocyst selected based on chromosomal assessment) in a uterus.

Also provided herein are methods of treating infertility by controlled ovarian stimulation in a patient predicted to have a high ovarian response to controlled ovarian stimulation, comprising selecting a patient identified as predicted to have a high ovarian response to controlled ovarian stimulation; conducting controlled ovarian stimulation by administering to the selected patient HP-hMG at a starting daily dose of 75 IU to 225 IU; at a mid-follicular stage of controlled ovarian stimulation, determining if the patient's serum level of hCG is at a target mid-follicular threshold level; and optionally, administering hCG to the patient based on whether the patient's serum level of hCG is at or below the target mid-follicular threshold level. The method may comprise administering hCG at a daily dose of, or equivalent to, 5-60 IU/day when the patient's serum level of hCG is below the target mid-follicular threshold level.

Also provided herein are methods of treating infertility by controlled ovarian stimulation in a patient predicted to have a high ovarian response to controlled ovarian stimulation, comprising selecting a patient identified as predicted to have a high ovarian response to controlled ovarian stimulation; conducting controlled ovarian stimulation by administering to the selected patient rFSH at a daily dose effective for controlled ovarian stimulation; starting at a mid-follicular stage of controlled ovarian stimulation, administering hCG to the patient at a daily dose of, or equivalent to, 5-60 IU/day.

Also provided herein are compositions comprising HP-hMG for use in the treatment of infertility in a patient predicted to have a high ovarian response to controlled ovarian stimulation, wherein the treatment comprises selecting a patient identified as predicted to have a high ovarian response to controlled ovarian stimulation; conducting controlled ovarian stimulation by administering a daily dose of HP-hMG to the patient from day one of treatment (e.g., from 75-450 IU/day, preferably from 75-225 IU/day, more preferably 150 or 225 IU/day, most preferably 150 IU/day); at a mid-follicular stage of controlled ovarian stimulation (e.g., at stimulation day 5 or 6 or 7), determining if the patient's serum level of hCG is at a target mid-follicular threshold level (e.g., ≥1.5 mIU/mL); and triggering final follicular maturation when the level of hCG in the patient's serum is at, or above, a specified threshold level of serum hCG at final follicular maturation which leads to an increased probability of live birth. The specified threshold level of serum hCG at final follicular maturation which leads to an increased probability of live birth may be selected from 1.5-2.0 mIU/mL, more preferably 1.8 mIU/mL.

Also provided herein are compositions comprising HP-hMG for use in the treatment of infertility in a patient predicted to have a high ovarian response to controlled ovarian stimulation to increase the probability of live birth following fresh or frozen embryo transfer, wherein the treatment comprises selecting a patient identified as predicted to have a high ovarian response to controlled ovarian stimulation; conducting controlled ovarian stimulation by administering a daily dose of HP-hMG to the patient from day one of treatment (e.g., from 75-450 IU/day, preferably from 75-225 IU/day, more preferably 150 or 225 IU/day, most preferably 150 IU/day); at a mid-follicular stage of controlled ovarian stimulation (e.g., at stimulation day 5 or 6 or 7), determining if the patient's serum level of hCG is at a target mid-follicular threshold level (e.g., ≥1.5 mIU/mL); and triggering final follicular maturation when the level of hCG in the patient's serum is at, or above, a specified threshold level of serum hCG at final follicular maturation which leads to an increased probability of live birth. The specified threshold level of serum hCG at final follicular maturation which leads to an increased probability of live birth may be selected from 1.5-2.0 mIU/mL, more preferably 1.8 mIU/mL.

Also provided herein are compositions comprising HP-hMG for use in the treatment of infertility in a patient predicted to have a high ovarian response to controlled ovarian stimulation, wherein the treatment comprises selecting a patient identified as predicted to have a high ovarian response to controlled ovarian stimulation; conducting controlled ovarian stimulation by administering a daily dose of HP-hMG to the selected patient from day one of treatment (e.g., from 75-450 IU/day, preferably from 75-225 IU/day, more preferably 150 or 225 IU/day, most preferably 150 IU/day); at a mid-follicular stage of controlled ovarian stimulation (e.g., at stimulation day 5 or 6 or 7), determining whether the patient's serum level of hCG is at a target mid-follicular threshold level (e.g., ≥1.5 mIU/mL); and, optionally, maintaining or increasing the daily dose of HP-hMG (e.g., by 75 IU/day) based on whether the patient's serum level of hCG is at or below the target mid-follicular threshold level.

Also provided herein are compositions comprising HP-hMG for use in the treatment of infertility in a patient predicted to have a high ovarian response to controlled ovarian stimulation to increase the probability of live birth following fresh or frozen embryo transfer, wherein the treatment comprises selecting a patient identified as predicted to have a high ovarian response to controlled ovarian stimulation; conducting controlled ovarian stimulation by administering a daily dose of HP-hMG to the selected patient from day one of treatment (e.g., from 75-450 IU/day, preferably from 75-225 IU/day, more preferably 150 or 225 IU/day, most preferably 150 IU/day); at a mid-follicular stage of controlled ovarian stimulation (e.g., at stimulation day 5 or 6 or 7), determining whether the patient's serum level of hCG is at a target mid-follicular threshold level (e.g., ≥1.5 mIU/mL); and, optionally, maintaining or increasing the daily dose of HP-hMG (e.g., by 75 IU/day) based on whether the patient's serum level of hCG is at or below the target mid-follicular threshold level.

In any of the compositions for use set forth herein, the patient may have a serum anti-Müllerian hormone (AMH) level≥35.7±0.5 pmol/L (≥5.0±0.2 ng/ml) prior to treatment/ stimulation; the treatment may further comprises, prior to stimulation, identifying the patient as having a serum anti-Müllerian hormone (AMH) level≥35.7±0.5 pmol/L (≥5.0±0.2 ng/ml); the patient is not an anovulatory patient; the patient is 21-35 years old, and/or the patient has a BMI of 18-30 kg/m² at the start of treatment.

In any of the HP-hMG compositions for use set forth herein, the composition may comprise 75 to 450 IU HP-hMG and the controlled ovarian stimulation may comprise administering HP-hMG at a starting dose of 75 to 225 IU hMG per day, preferably 150 IU/day, e.g. from day 1 to at least day 5 of stimulation.

In any of the HP-hMG compositions for use set forth herein, the treatment of infertility may increase the probability of live birth compared to treatment with CHO cell-derived recombinant FSH.

In any of the compositions for use set forth herein, the treatment may further comprise triggering final follicular maturation by administering hCG or a GnRH agonist, optionally supplemented with hCG, and/or administering a GnRH antagonist starting on day 6 of stimulation.

In any of the compositions for use set forth herein, the treatment may further comprise (a) retrieving oocyte(s), fertilizing the oocyte(s), allowing the fertilized oocyte(s) to develop to the blastocyst stage, optionally assessing the quality/morphology of the blastocyst(s), and implanting a fresh blastocyst (optionally selected based on, e.g., visual assessment of quality/morphology) in a uterus; or (b) retrieving oocyte(s), fertilizing the oocyte(s), allowing the fertilized oocyte(s) to develop to the blastocyst stage, optionally assessing chromosomal quality of the blastocyst(s), freezing one or more or all blastocyst(s), and implanting a thawed-frozen blastocyst (e.g., a euploid blastocyst selected based on chromosomal assessment) in a uterus; or (c) retrieving oocyte(s), freezing unfertilized oocytes(s), subsequently thawing one or more oocyte(s), fertilizing one or more or all thawed oocyte(s), allowing fertilized oocyte(s) to develop to the blastocyst stage, optionally assessing the quality/morphology of the blastocyst(s), and implanting a blastocyst (optionally selected based on, e.g., visual assessment of quality/morphology) in a uterus; or (d) retrieving oocyte(s), freezing unfertilized oocytes(s), subsequently thawing one or more frozen oocytes, fertilizing one or more or all thawed oocyte(s), allowing fertilized oocyte(s) to develop to the blastocyst stage, optionally assessing chromosomal quality of the blastocyst(s), freezing one or more or all blastocyst(s), and implanting a thawed-frozen blastocyst (e.g., a euploid blastocyst selected based on chromosomal assessment) in a uterus.

Also provided is a composition comprising HP-hMG for use in the treatment of infertility as described herein. Also provided is a composition comprising hCG for use in the treatment of infertility as described herein. Also provided is a composition comprising rFSH for use in the treatment of infertility as described herein.

Also provided is HP-hMG for use in the preparation of a medicament for treating infertility as described herein. Also provided is hCG for use in the preparation of a medicament for treating infertility as described herein. Also provided is rFSH for use in the preparation of a medicament for treating infertility as described herein.

The foregoing general description is exemplary and explanatory and intended to provide further explanation of the invention. For detailed understanding of the invention, reference is made to the following detailed description. Other objects, advantages and novel features will be readily apparent to those skilled in the art from the following detailed description.

DETAILED DESCRIPTION

Described herein are assisted reproductive technology methods, e.g., methods for treating infertility. In particular, described herein are controlled ovarian stimulation (COS) methods that may be particularly useful for women predicted to have a high ovarian response to controlled ovarian stimulation. As shown in Example 1, the methods are useful for increasing the probability of live birth, e.g., for increasing live birth rates.

The present invention is based on the unexpected finding by the inventors that, in subjects predicted to be high responders, serum hCG on the last day of controlled ovarian stimulation is a significant predictor of the probability of live birth, with higher serum hCG being correlated with a higher chance of live birth. As reported in Example 1 below, for every 1 mIU/mL increase in hCG, the odds of live birth in HP-hMG treated subjects increased by 38%. This is the first report of such an effect in predicted high responders. Arce and Smitz, *Human Fertility,* 14(3): 192-99 (2011), reports a retrospective analysis of normogonadotropic anovulatory infertility patients treated with HP-hMG or rFSH (GONAL-F) in a low-dose step-up protocol that found serum hCG at the end of stimulation to be positively associated with treatment outcome in the normogonadotropic anovulatory patients. Arce and Smitz, *Gynecol. Endocrinol.* 29(1): 46-50 (2013), reports a retrospective analysis of the HP-hMG arm of a long GnRH agonist protocol in women with regular menstrual cycles of 21-35 days and tubal-factor or unexplained infertility or partners with mild semen abnormalities that found serum hCG at stimulation day 6 to be positively associated with treatment outcome in that patient subgroup. Prior to the present invention, however, no impact of serum hCG on treatment outcome has been predicted or reported for ovulating women predicted to have a high ovarian response to controlled ovarian stimulation.

Thus, in accordance with some aspects, described herein are compositions and methods for increasing the probability of live birth by targeting a threshold serum hCG level on the last day of stimulation through HP-hMG dosing, such as by determining serum hCG at a mid-follicular stage of stimulation with HP-hMG, and adjusting HP-hMG dosing to achieve a target serum hCG level on the last day of stimulation. While not wanting to be bound by theory, the results discussed herein suggest that hCG derived from (e.g., provided by) HP-hMG contributes positively to the likelihood of live birth when used in controlled ovarian stimulation of predicted high responders, particularly as compared to patients treated with CHO cell-derived rFSH as the gonadotropin.

Also described herein are compositions and methods for increasing the probability of live birth by targeting a threshold serum hCG level on the last day of stimulation through hCG dosing, such as by administering hCG starting at a mid-follicular stage of controlled ovarian stimulation with HP-hMG or rFSH, to achieve a target serum hCG level on the last day of stimulation.

Definitions

Technical and scientific terms used herein have the meanings commonly understood by one of ordinary skill in the art of assisted reproductive technology to which the present invention pertains, unless otherwise defined. Reference is made herein to various methodologies known to those of ordinary skill in the art. Unless otherwise specified, any suitable materials and/or methods known to those of ordinary skill in the art can be utilized in carrying out the present invention. However, specific materials and methods are described. Materials, reagents and the like to which reference is made in the following description and examples are obtainable from commercial sources, unless otherwise noted.

As used herein, the singular forms "a," "an," and "the" designate both the singular and the plural, unless expressly stated to designate the singular only.

As used herein, the term "about" means that the number or range is not limited to the exact number or range set forth, but encompass ranges around the recited number or range as will be understood by persons of ordinary skill in the art depending on the context in which the number or range is used. Unless otherwise apparent from the context or convention in the art, "about" mean up to plus or minus 10% of the particular term.

As used herein, the term "anovulatory" or "anovulation" refers to a patient whose ovaries do not release an oocyte during a menstrual cycle. Therefore, ovulation does not take place. Chronic anovulation is a common cause of infertility. In general, the patient for the compositions and methods described herein is not an anovulatory patient.

As used herein "ongoing pregnancy" refers to pregnancy with a viable fetus and detectable fetal heartbeat at 10-11 weeks gestation, e.g., at 8-9 weeks post blastocyst/embryo transfer.

As used herein "clinical pregnancy" refers to gestation and a detectable fetal heartbeat at 5-6 weeks gestation, e.g., at 3-4 weeks post blastocyst/embryo transfer.

As used herein, "woman" refers to an adult female human. Typically, a woman treated in accordance with the compositions and methods described herein is 35 years old or younger, has a serum level of anti-Müllerian hormone $(AMH) \geq 35.7 \pm 0.5$ pmol/L $(\geq 5.0 \pm 0.2$ ng/ml) when measured using a Beckmann-Coulter Gen 2 assay as described in Arce et al., *Fertility and Sterility* 99: 1644-53 (2013), or an equivalent AMH level assessed by a different method, and a BMI of 30 kg/m$^2$ or less. In some embodiments, a woman treated in accordance with the compositions and methods described herein is identified, prior to treatment, as being 21-35 years old. In some embodiments, a woman treated in accordance with the compositions and methods described herein is identified, prior to treatment, as being 35 years old or younger, or 34 years old or younger. In some embodiments, a woman treated in accordance with the methods described herein is identified, prior to treatment, as being 21-34 years old, or 21-33 years old, or 21-32 years old, or 21-31 years old. In some embodiments, a woman treated in accordance with the methods described herein is identified, prior to treatment, as having a BMI of 18-30 kg/m$^2$. In some embodiments, a woman treated in accordance with the methods described herein is identified, prior to treatment, as having a BMI of 38 kg/m$^2$ or less, 36 kg/m$^2$ or less, 34 kg/m$^2$ or less, 32 kg/m$^2$ or less, 30 kg/m$^2$ or less, or 28 kg/m$^2$ or less, such as BMI of 18-38, 18-36, 18-34, 18-32, 18-30, or 18-28 kg/m$^2$. In some embodiments, a woman treated in accordance with the methods described herein is identified as having a BMI of 18-25 kg/m$^2$, 18-26 kg/m$^2$, 18-27 kg/m$^2$, 18-28 kg/m$^2$, 18-29 kg/m$^2$, or 18-30 kg/m$^2$.

As used herein, subjects classified as being "predicted to have a high ovarian response to controlled ovarian stimulation" or as a "predicted high responder" refers to women who are likely to develop high numbers of follicles or oocytes following a standard protocol of controlled ovarian stimulation (COS), such as women with a greater than average likelihood of producing 15 or more oocytes. Women may be identified as being predicted high responders if they have generated 15 or more oocytes in a previous ART cycle, e.g., in a previous COS treatment. Additionally or alternatively, women may be identified as being predicted high responders if they are considered to be at risk of developing OHSS. Additionally or alternatively, women may be identified as being predicted high responders if they have a serum level of anti-Müllerian hormone $(AMH) \geq 35.7 \pm 0.5$ pmol/L $(\geq 5.0 \pm 0.2$ ng/ml), such as a serum AMH level$\geq 35.7 \pm 0.5$ pmol/L $(\geq 5.0 \pm 0.2$ ng/ml), when measured using a Beckmann-Coulter Gen 2 assay as described in Arce et al., *Fertility and Sterility* 99: 1644-53 (2013), or an equivalent AMH level assessed by a different method.

The term "menotropin" as used herein includes human menopausal gonadotropin or "hMG," including "highly purified menotropin" or "HP-hMG." As used herein, the terms "highly purified menotropin" and "HP-hMG" refer to a highly purified hMG product that includes both follicle stimulating hormone (FSH) and human chorionic gonadotropin (hCG)-driven luteinizing hormone (LH) activity, including hMG products wherein most of the LH activity is provided by hCG, including products wherein $\geq 90\%$, or $\geq 95\%$, of the LH activity is provided by hCG. See, e.g., Foutouh et al., *Reproductive BioMed. Online,* 14(2): 145-47 (2007); Wolfenson et al., *Reprod. BioMed. Online,* 10(4): 442-54 (2005). In some embodiments, the HP-hMG is the HP-hMG product available under the trademark MENOPUR® from Ferring Pharmaceuticals, Inc., which contains FSH and hCG-driven LH activity, wherein $\geq 95\%$, of the LH activity is provided by hCG (pituitary hCG), as assessed by immunoreactivity. See, e.g., Arce and Smitz, *Human Fertility,* 14(3): 192-99 (2011). As reconstituted for use, one vial of MENOPUR® (75 IU HP-hMG) contains 75 IU FSH activity and 75 IU LH activity, wherein hCG contributes about 70 IU of the LH activity.

The term "GnRH agonist" as used herein includes gonadotropin-releasing hormone (GnRH) agonists such as buserelin (e.g., SUPRECUR®), leuprorelin (e.g., leuprolide acetate, e.g., LUPRON®), nafarelin (e.g., SYNAREL®), and triptorelin (e.g., TRELSTAR®).

The term "GnRH antagonist" as used herein includes gonadotropin-releasing hormone (GnRH) antagonists, such as ganirelix acetate (e.g., ORGALUTRAN®) and cetrorelix acetate (e.g., CETROTIDE®), which block the action of GnRH by competitive blocking of the GnRH receptors on pituitary gonadotropes, and thus prevent gonadotropin production/release and premature ovulation (release of eggs).

As used herein, the phrase "effective amount" refers to a dosage determined to provide the specific pharmacological effect for which the drug is administered in a subject in need of such treatment. It is emphasized that a therapeutically effective amount will not always be effective in treating the conditions described herein in a given patient, even though such dosage is deemed to be a therapeutically effective amount by those of skill in the art. For convenience only, exemplary dosages and therapeutically effective amounts are provided below with reference to adult female human subjects. Those skilled in the art can adjust such amounts in accordance with standard practices as needed to treat a specific subject and/or condition/disease.

Assisted Reproductive Technology Methods

The treatment methods described herein are useful in any reproductive technology methods that involve controlled ovarian stimulation (COS), such as for in vitro fertilization, including in vitro fertilization by intra-cytoplasmic sperm injection (ICSI), methods involving fresh transfer of fertilized eggs (e.g., blastocysts/embryos), methods involving freezing fertilized eggs for later implantation, and methods involving freezing unfertilized oocytes for later fertilization.

As noted above, in accordance with some aspects, the present invention provides reproductive technology methods that involve using a highly purified menotropin (HP-hMG) product that includes both FSH and hCG-driven LH activity as the gonadotropin for COS in women who are predicted to have a high ovarian response to COS and undergoing COS. As also noted above, for the purposes of the compositions and methods disclosed herein, women may be identified as being predicted to have a high ovarian response to COS based on having a high ovarian response in a previous ART cycle, e.g., in a previous COS treatment, or if they have a serum level of anti-Müllerian hormone (AMH)≥35.7±0.5 pmol/L (≥5.0±0.2 ng/ml), such as a serum AMH level≥35.7±0.5 pmol/L (≥5.0±0.2 ng/ml) when measured using a Beckmann-Coulter Gen 2 assay as described in Arce et al., *Fertility and Sterility* 99: 1644-53 (2013), or an equivalent AMH level assessed by a different method. Serum levels of AMH are a surrogate marker for functional ovarian follicle reserve, and a positive correlation between serum levels of AMH and ovarian response (e.g., oocyte yield) have been reported. Id. In accordance with the compositions and methods described herein, women typically are identified as being predicted high responders based on serum AMH level.

Thus, in accordance with some aspects, an assisted reproductive technology treatment method as described herein comprises conducting controlled ovarian stimulation in a woman predicted to have a high ovarian response to controlled ovarian stimulation using HP-hMG to stimulate follicle development, determining serum hCG during stimulation, and adjusting HP-hMG dosing to achieve a target serum hCG on the last day of stimulation. More specifically, the compositions and methods described herein relate to the treatment of infertility by controlled ovarian stimulation in a patient predicted to have a high ovarian response to controlled ovarian stimulation, comprising selecting a patient identified as predicted to have a high ovarian response to controlled ovarian stimulation; conducting controlled ovarian stimulation by administering to the selected patient HP-hMG at a starting daily dose of, for example, 75 IU to 225 IU; at a mid-follicular stage of controlled ovarian stimulation, determining if the patient's serum level of hCG is at a target mid-follicular threshold level; and optionally, maintaining or increasing the daily dose of HP-hMG based on whether the patient's serum level of hCG is at or below the target mid-follicular threshold level. In any embodiments described herein, the HP-hMG may be MENOPUR®.

The treatment methods may comprise, prior to conducting controlled ovarian stimulation, identifying the patient (e.g., woman) as predicted to have a high ovarian response to controlled ovarian stimulation, such as by having a serum AMH level greater than or equal to 35.7±0.5 pmol/L (≥5.0±0.2 ng/ml), when measured using a Beckmann-Coulter Gen 2 assay, or a comparable AMH level measured by a different method. Thus, an assisted reproductive technology treatment method as described herein may comprise selecting a woman identified as predicted to have a high ovarian response to controlled ovarian stimulation and conducting controlled ovarian stimulation as summarized above and described in more detail below. The method may further comprise, prior to conducting controlled ovarian stimulation, determining the woman is predicted to have a high ovarian response to controlled ovarian stimulation, such as by determining the woman has a serum AMH level greater than or equal to 35.7±0.5 pmol/L (≥5.0±0.2 ng/ml), when measured using a Beckmann-Coulter Gen 2 assay, or a comparable AMH level measured by a different method. In any embodiments, the woman may have, or be identified as having a serum AMH level greater than or equal to 35.7±0.5 pmol/L (≥5.0±0.2 ng/ml), when measured using a Beckmann-Coulter Gen 2 assay, or a comparable AMH level measured by a different method. In any embodiments, the patient (e.g., woman) is not an anovulatory woman.

In accordance with some aspects, the methods include administering HP-hMG to the subject in an amount effective to stimulate follicle development, for example, from about 75 IU/day to about 450 IU/day, including 150 IU/day or 225 IU/day. The HP-hMG administration typically is commenced on day 2 or day 3 of the patient's menstrual cycle, such that treatment day 1 (also referred to herein as stimulation day 1) occurs on day 2 or day 3 of the patient's menstrual cycle. Administration of HP-hMG continues daily until the desired level of follicle production is reached, for a total stimulation period of from about 1 to about 20 days, typically for a total stimulation period of from 8 to 12 days, more specifically typically for about 9-11 days, including for about 10 days.

HP-hMG may be administered at a dose of from about 75 IU/day to about 450 IU/day, including 75 IU/day, 150 IU/day, 225 IU/day, 300 IU/day, 375 IU/day or 450 IU/day, which may be adjusted during the stimulation period. Typically, a starting dose of HP-hMG is 150 IU/day, but may range from 75 IU/day to 225 IU/day. Pharmaceutical compositions comprising HP-hMG are available commercially, such as the MENOPUR® product sold by Ferring Pharmaceuticals, Inc., which is formulated for subcutaneous injection.

It is known in the art to adjust gonadotropin dosing (e.g., increase or decrease HP-hMG or rFSH dosing) during the stimulation period based on the subject's ovarian (follicular) response, which may be assessed, for example, by transvaginal ultrasound (TVUS), and serum estradiol levels. For example, it is known to adjust gonadotropin dosing during the stimulation period when one or both of the patient's serum estradiol level and number of follicles>12 mm are either too low or too high. Such an assessment and adjustment may be made at any time during the stimulation period, typically during a mid-follicular stage of stimulation, typically on the 5$^{th}$ or 6$^{th}$ or 7$^{th}$ day of stimulation.

In accordance with some aspects of the compositions and methods disclosed herein, HP-hMG dosing is (additionally or alternatively) adjusted during the stimulation period (e.g., at a mid-follicular stage of stimulation) based on the patient's serum hCG level. Thus, the patient's serum hCG level is determined during the stimulation period (e.g., at a mid-follicular stage of stimulation) and, if the serum hCG is below a target level (e.g., below a target mid-follicular level), the HP-hMG dose is increased (e.g., as long as an increased dose is not contraindicated by other safety factors, such as high ovarian response). Such an assessment and adjustment may be made at any time during the stimulation period that will impact serum hCG on the last day of stimulation, such as at a mid-follicular stage of stimulation, typically after 4-6 days of stimulation, such as on the 5$^{th}$ or 6$^{th}$ or 7$^{th}$ day of stimulation, including on stimulation day 6.

Serum hCG may be determined by any means known in the art, including by enzyme-linked immunosorbent assay (ELISA) or electrochemiluminescence immunoassay, as is known in the art. In some embodiments, serum hCG is measured by an ELISA with a lower detection limit for hCG of 0.5 mIU/mL. In some embodiments, serum hCG is measured by an electrochemiluminescence immunoassay with a lower detection limit for hCG of 0.1 mIU/mL. Serum hCG typically is measured using a blood sample taken from the patient at least 8 hours after the most recent dose of HP-hMG was administered.

In accordance with the compositions and methods described herein, the target threshold serum hCG on the last day of stimulation may be from 1.5 to 2.0 mIU/mL. The target mid-follicular serum hCG threshold level is selected to achieve the target last day serum hCG threshold level on the last day of stimulation. In some embodiments, the target threshold serum hCG on the last day of stimulation is ≥1.8 mIU/mL (1.8 IU/L). Consistent with such embodiments, the target mid-follicular serum hCG (e.g., on stimulation day 5 or 6 or 7) is selected to achieve the target last day threshold serum hCG by the last day of stimulation, and thus may be, for example, ≥1.4 mIU/mL, ≥1.5 mIU/mL, ≥1.6 mIU/mL, or ≥1.7 mIU/mL, such as ≥1.5 mIU/mL. In some embodiments, the target threshold serum hCG on the last day of stimulation is ≥2.0 mIU/mL (2.0 IU/L). Consistent with such embodiments, the target mid-follicular serum hCG (e.g., on stimulation day 5 or 6 or 7) may be, for example, ≥1.6 mIU/mL, ≥1.7 mIU/mL, ≥1.8 mIU/mL, or ≥1.9 mIU/mL, selected to achieve the target last day threshold serum hCG by the last day of stimulation. In some embodiments, the target threshold serum hCG on the last day of stimulation is ≥1.5 mIU/mL (1.5 IU/L). Consistent with such embodiments, the target mid-follicular serum hCG (e.g., on stimulation day 5 or 6 or 7) may be, for example, ≥1.2 mIU/mL, ≥1.3 mIU/mL, or ≥1.4 mIU/mL, selected to achieve the target last day threshold serum hCG by the last day of stimulation. In specific embodiments, the target threshold serum hCG on the last day of stimulation is ≥1.8 mIU/mL (1.8 IU/L), and the target mid-follicular serum hCG (e.g., on stimulation day 5 or 6 or 7) is ≥1.5 mIU/mL.

Thus, in accordance with some aspects, an assisted reproductive technology treatment method as described herein comprises conducting controlled ovarian stimulation in an identified predicted high responder by administering a daily dose of HP-hMG effective to stimulate follicle development, and, at a mid-follicular stage of the stimulation period (such as, for example, on stimulation day 6), determining whether the patient's serum hCG level is at a target mid-follicular threshold level (such as ≥1.5 mIU/mL), and, optionally, maintaining or increasing the daily dose of HP-hMG based on whether the patient's serum hCG level is at the target mid-follicular threshold level (such as increasing the daily dose of HP-hMG if the patient's serum hCG level is below the target mid-follicular threshold level). The daily dose of HP-hMG may be increased in increments of, e.g., 37.5 IU/day or 75 IU/day, typically in increments of 75 IU/day. The increased daily dose may be continued throughout the remainder of the stimulation period (e.g., as long as continuing the increased dose is not contraindicated by other safety factors, such as high ovarian response).

In some embodiments, the patient's serum hCG level may be determined again (e.g., 1-3 days after the first determination) and, the method may further comprise optionally maintaining or increasing the daily dose of HP-hMG based on whether the patient's serum hCG level is at a target level, wherein the target level for the subsequent determination is selected to achieve the target last day threshold serum hCG by the last day of stimulation (such as ≥1.5, or ≥1.6, or ≥1.7 mIU/mL for a target last day threshold of 1.8 mIU/mL). The daily dose of HP-hMG may be increased in increments of, e.g., 37.5 IU/day or 75 IU/day, typically in increments of 75 IU/day. The increased daily dose may be continued throughout the remainder of the stimulation period (e.g., as long as continuing the increased dose is not contraindicated by other safety factors, such as high ovarian response).

Optionally, the treatment methods may comprise determining serum hCG level at other stages of the stimulation period, including prior to stimulation and/or at the last day of stimulation.

By determining serum hCG level at a mid-follicular stage of the stimulation period and increasing the daily dose of HP-hMG if the serum hCG level is below a target mid-follicular threshold level, the treatment methods described herein are designed to achieve a target threshold serum hCG level on the last day of stimulation, which the present inventors have determined to be significantly predictive of live birth. Indeed, based on the results reported in Example 1, it was surprisingly and unexpectedly determined that predicted high responder patients with a serum hCG≥1.8 mIU/mL on the last day of stimulation had a greater than 85% probability of live birth, while patients with a serum hCG<1.8 mIU/mL on the last day of stimulation had a less than 25% probability of live birth. Additionally, as reported in Example 1 below, it was surprisingly and unexpectedly found that every 1 mIU/mL increase in serum hCG on the last day of stimulation increased the chance of live birth by 38%.

In accordance with known protocols, the gonadotropin (e.g., HP-hMG) is administered daily until the desired level of follicle production is reached. For example, the gonadotropin (e.g., HP-hMG) may be administered until three follicles have developed with a diameter of ≥17 mm, as may be determined by TVUS. Typically, the maximum gonadotropin dosing period (stimulation period) is 20 days, with a typical dosing period of 8-12 days, more specifically typically about 9-11 days, including about 10 days.

In some embodiments, the treatment methods include the administration of a GnRH antagonist during a portion of the period of gonadotropin (e.g., HP-hMG) administration. For example, a GnRH antagonist may be administered once the lead follicle reaches 14 mm in diameter, and continued through the remainder of the period of gonadotropin (e.g., HP-hMG) administration. For example, a GnRH antagonist may be administered starting on the 5$^{th}$ or 6$^{th}$ or 7$^{th}$ day of stimulation (e.g., stimulation day 6), and continued through the remainder of the period of gonadotropin (e.g., HP-hMG) administration. When the GnRH antagonist is ganirelix acetate (such as ORGALUTRAN®), a typical dose is 0.25 mg/day administered subcutaneously.

In other embodiments, the treatment methods include the administration of a GnRH agonist prior to conducting controlled ovarian stimulation, such as the administration of triptorelin (typically at 0.1 mg/day subcutaneously) or leuprorelin (e.g., leuprolide acetate, e.g., LUPRON®) prior to conducting controlled ovarian stimulation.

In some embodiments, the treatment methods further comprise triggering final follicular maturation. For example, once the desired level of follicle production is reached, trigger of final follicular maturation can be stimulated by methods known in the art, such as by a bolus injection of human chorionic gonadotropin (hCG). For example, trigger of final follicular maturation may be stimulated in a patient with ≥3 follicles of ≥17 mm in diameter each, and, typically, estradiol (E2) levels<10,000 pmol/mL. Thus, in some embodiments, the treatment methods may comprise administering hCG to trigger final follicular maturation. The dose of hCG may be 5,000 IU to 10,000 IU. A typical dose of recombinant hCG (such as OVITRELLE®, Merck) is 250 μg (6,500 IU of hCG activity), usually administered by a single subcutaneous injection.

A GnRH agonist may be used as an alternative to use of hCG to trigger final follicular maturation. Thus, in some embodiments, the treatment methods may comprise administering a gonadotropin releasing hormone (GnRH agonist) to trigger final follicular maturation. A GnRH agonist may be used to trigger final follicular maturation, for example, in the event of excessive response, such as in a patient who, after COS treatment, has >25 follicles≥12 mm in diameter or serum estradiol (E2) levels≥5,000 pmol/L, or has >30 follicles≥12 mm in diameter or serum estradiol (E2) levels≥5,000 pmol/L, or estradiol (E2) levels≥10,000 pmol/L, or ≥20 follicles≥12 mm in diameter or estradiol (E2) levels≥15,000 pmol/L. The GnRH agonist may be leuprolide acetate, e.g., LUPRON®, typically used at a dose of, e.g. 1-4 mg. The GnRH agonist may be triptorelin acetate, e.g., DECAPEPTYL®, typically used at a dose of, e.g., 0.2 mg. When a GnRH agonist is used to trigger final follicular maturation, a small amount of hCG also may be used, such as, for example 500-3000 IU hCG. When a GnRH agonist is used to trigger final follicular maturation, a "freeze all" protocol (discussed below) typically is followed, e.g., for safety reasons.

In some embodiments, the treatment methods further comprise retrieving oocytes and fertilizing the oocytes by methods known in the art, such as ICSI.

In some embodiments, the treatment method is a fresh transfer method. For fresh transfer methods, one or more blastocysts are selected for transfer. Remaining blastocysts can be frozen by methods known in the art for future transfer (including vitrification). Thus, in fresh transfer embodiments the methods comprise retrieving oocyte(s), fertilizing the oocyte(s), allowing the fertilized oocyte(s) to develop to the blastocyst stage, retrieving blastocyst(s), optionally selecting a blastocyst(s) based on assessment of quality/morphology, and implanting a fresh blastocyst (optionally selected based on, e.g., assessment of quality/morphology) in a uterus. In specific embodiments, the compositions and methods described herein are used in a single blastocyst transfer protocol, wherein a single blastocyst is selected for fresh transfer. In accordance with those embodiments, remaining blastocysts can be frozen by methods known in the art for future transfer.

In some embodiments, the method is a frozen transfer method. In frozen transfer embodiments, the methods comprise retrieving oocyte(s), fertilizing the oocyte(s), allowing the fertilized oocyte(s) to develop to the blastocyst stage, optionally assessing chromosomal quality of the blastocyst(s), freezing one or more or all blastocyst(s), and implanting a thawed-frozen blastocyst (e.g., a euploid blastocyst selected based on chromosomal assessment) in a uterus. For frozen and "freeze all" methods, selected blastocysts are frozen by methods known in the art for future implantation/transfer.

In some embodiments, unfertilized oocytes are frozen. In such embodiments, the methods comprise retrieving oocyte(s) and freezing one or more or all retrieved oocytes for future fertilization by methods known in the art. In such embodiments, the methods may subsequently comprise thawing one or more frozen oocytes, fertilizing the oocyte(s), allowing the fertilized oocyte(s) to develop to the blastocyst stage, optionally selecting blastocyst(s) based on assessment of quality/morphology, and implanting a blastocyst (optionally selected based on, e.g., visual assessment of quality/morphology) in a uterus. Alternatively, the methods may comprise retrieving oocyte(s), freezing one or more or all retrieved oocytes for future fertilization, subsequently thawing one or more frozen oocytes, fertilizing the oocyte(s), allowing the fertilized oocyte(s) to develop to the blastocyst stage, conducting chromosomal assessment of blastocyst(s), freezing blastocyst(s), and implanting a thawed-frozen blastocyst (e.g., a euploid blastocyst selected based on chromosomal assessment) in a uterus.

As noted above, in some embodiments, the methods comprise assessing chromosomal quality of the blastocyst(s) or selecting blastocyst(s) based on chromosomal assessment. This may be done by methods known in the art, such as Preimplantation Genetic Testing for Aneuploidy (PGT-A also known as PGS) or Preimplantation Genetic Diagnosis (PGD), which is used to test blastocysts (embryos) for genetic and chromosomal information. When PGS or PGD is used, all chromosomes can be assessed and only blastocysts identified at low risk of chromosome abnormalities are selected for embryo transfer (implantation in a uterus). This is an alternative to traditional methods where embryos are chosen according to their appearance under the microscope after three or five days of development in an incubator.

As set forth above, the compositions and methods described herein are useful for increasing probability of live birth, e.g., after in vitro fertilization and fresh or frozen transfer, particularly as compared to comparable methods using CHO cell-derived recombinant follicle stimulating hormone (rFSH) (e.g., GONAL-F, EMD Serono) as the gonadotropin.

Thus, according to some embodiments, there are provided methods of treating infertility by controlled ovarian stimulation in a patient predicted to have a high ovarian response to controlled ovarian stimulation, comprising selecting a patient identified as predicted to have a high ovarian response to controlled ovarian stimulation; conducting controlled ovarian stimulation by administering to the selected patient HP-hMG at a starting daily dose of, for example, 75 IU to 225 IU, such as 150 IU/day; at a mid-follicular stage of controlled ovarian stimulation (e.g., selected from stimulation day 5 or 6 or 7), determining whether the patient's serum level of hCG is at a target mid-follicular threshold level (such as ≥1.5 mIU/mL); and, optionally, maintaining or increasing the daily dose of HP-hMG (such as by 75 IU/day) based on whether the patient's serum level of hCG is at the target mid-follicular threshold level. Also provided are methods of increasing the probability of live birth after in vitro fertilization and fresh or frozen transfer in a patient predicted to have a high ovarian response to controlled ovarian stimulation, comprising selecting a patient identified as predicted to have a high ovarian response to controlled ovarian stimulation; conducting controlled ovarian stimulation by administering to the selected patient HP-hMG at a starting daily dose of, for example, 75 IU to 225 IU, such as 150 IU/day; at a mid-follicular stage of controlled ovarian stimulation (e.g., selected from stimulation day 5 or 6 or 7), determining whether the patient's serum level of hCG is at a target mid-follicular threshold level (such as ≥1.5 mIU/mL); and, optionally, maintaining or increasing the daily dose of HP-hMG (such as by 75 IU/day) based on whether the patient's serum level of hCG is at the target mid-follicular threshold level. As discussed above, the patient may have a serum anti-Müllerian hormone (AMH) level greater than or equal to 35.7±0.5 pmol/L (≥5.0±0.2 ng/ml); optionally, the method may further comprise determining that the patient has a serum anti-Müllerian hormone (AMH) level greater than or equal to 35.7±0.5 pmol/L (≥5.0±0.2 ng/ml). As discussed above, the method may further comprise administering a gonadotropin-releasing hormone antagonist (GnRH antagonist), e.g., starting on day 6 of stimulation. As discussed above, the method may further comprise triggering final follicular maturation by administering human chorionic gonadotropin (hCG) or a gonadotropin-releasing hormone agonist (GnRH agonist) (optionally supplemented with hCG). As discussed above, the method may be a fresh transfer method further comprising retrieving oocyte(s), fertilizing the oocyte(s), allowing the fertilized oocyte(s) to develop to the blastocyst stage, retrieving blastocyst(s), optionally selecting a blastocyst based on assessment of quality/morphology, and implanting a fresh blastocyst in a uterus. Alternatively, the method may be a frozen transfer method further comprising retrieving oocyte(s), fertilizing the oocyte(s), allowing the fertilized oocyte(s) to develop to the blastocyst stage, optionally assessing chromosomal quality of blastocyst(s), freezing one or more or all blastocyst(s), and implanting a thawed frozen blastocyst (e.g., a euploid blastocyst selected based on chromosomal assessment) in a uterus. Alternatively, the method may comprise retrieving oocyte(s), freezing one or more or all unfertilized oocyte(s), subsequently thawing one or more frozen oocyte(s), fertilizing the oocyte(s), allowing the fertilized oocyte(s) to develop to the blastocyst stage, optionally selecting blastocyst(s) based on assessment of quality/morphology, and implanting a blastocyst (optionally selected based on, e.g., visual assessment of quality/morphology) in a uterus. Alternatively, the methods may comprise retrieving oocyte(s), freezing one or more or all unfertilized oocytes, subsequently thawing one or more frozen oocyte(s), fertilizing the oocyte(s), allowing the fertilized oocyte(s) to develop to the blastocyst stage, conducting chromosomal assessment of blastocyst(s), freezing blastocyst(s), and implanting a thawed-frozen blastocyst (e.g., a euploid blastocyst selected based on chromosomal assessment) in a uterus.

According to the present invention there also is provided a composition (e.g., a pharmaceutical composition) comprising HP-hMG for use in the treatment of infertility in a patient (e.g., a woman) predicted to have a of high ovarian response to controlled ovarian stimulation, wherein the treatment comprises selecting a patient identified as predicted to have a high ovarian response to controlled ovarian stimulation; conducting controlled ovarian stimulation by administering a daily dose of HP-hMG to the selected patient from day one of treatment (e.g. from day 2 or day 3 of the patients menstrual cycle); at a mid-follicular stage of controlled ovarian stimulation, determining if the patient's serum level of hCG is at a target mid-follicular threshold level (such as ≥1.5 mIU/mL); and triggering final follicular maturation when the level of hCG in the patient's serum is at, or above, a specified threshold level of serum hCG which leads to an increased probability of live birth. The specified threshold level of serum hCG at final follicular maturation which leads to an increased probability of live birth may be from 1.5 to 2 mIU/mL, more preferably 1.8 mIU/mL.

According to the present invention there is also provided a composition (e.g. a pharmaceutical composition) comprising HP=hMG for use in the treatment of infertility in a patient (e.g. a woman) predicted to have a high ovarian response to controlled ovarian stimulation to increase the probability of live birth following fresh or frozen embryo transfer, wherein the treatment comprises selecting a patient identified as predicted to have a high ovarian response to controlled ovarian stimulation; conducting controlled ovarian stimulation by administering a daily dose of HP-hMG to the patient from day one of treatment (e.g. from day 2 or day 3 of the patients menstrual cycle); at a mid-follicular stage of controlled ovarian stimulation, determining if the patient's serum level of hCG is at a target mid-follicular threshold level (such as ≥1.5 mIU/mL); and triggering final follicular maturation when the level of hCG in the patient's serum is at, or above, a specified threshold level of serum hCG which leads to an increased probability of live birth. The specified threshold level of serum hCG at day of trigger of final follicular maturation which leads to an increased probability of live birth may be from 1.5 to 2 mIU/mL. more preferably 1.8 mIU/mL.

According to the present invention there also is provided a composition (e.g., a pharmaceutical composition) comprising HP-hMG for use in the treatment of infertility in a patient (e.g., a woman) predicted to have a high ovarian response to controlled ovarian stimulation, wherein the treatment comprises selecting a patient identified as predicted to have a high ovarian response to controlled ovarian stimulation; conducting controlled ovarian stimulation by administering a daily dose of HP-hMG to the selected patient from day one of treatment (e.g., from day 2 or day 3 of the patients menstrual cycle); at a mid-follicular stage of controlled ovarian stimulation, determining whether the patient's serum level of hCG is at a target mid-follicular threshold level; and, optionally, maintaining or increasing the daily dose of HP-hMG (e.g., by an increments of 75 IU/day) based on whether the patient's serum level of hCG is at or below the target mid-follicular threshold level. The target mid-follicular level of serum hCG may be from 1.3 to 1.7 mIU/mL, and more preferably is 1.5 mIU/mL.

The patient may have a serum anti-Müllerian hormone (AMH) level≥35.7±0.5 pmol/L (≥5.0±0.2 ng/ml) prior to treatment/stimulation. The treatment may comprise a further step of identifying a patient having a serum anti-Müllerian hormone (AMH) level≥35.7±0.5 pmol/L (≥5.0±0.2 ng/ml), such as an AMH level≥35.7±0.5 pmol/L (≥5.0±0.2 ng/ml) when measured using a Beckmann-Coulter Gen 2 assay as described in Arce et al., *Fertility and Sterility* 99: 1644-53 (2013), or an equivalent AMH level assessed by a different method, prior to treatment/stimulation.

In examples of the invention, the patient is not an anovulatory patient.

The composition may comprise 75 to 450 IU HP-hMG, such as MENOPUR®. The treatment of infertility may comprise administering (to the patient) a dose of 75 to 450 IU HP-hMG per day, including 75 IU/day, 150 IU/day, 225 IU/day, 300 IU/day, 375 IU/day or 450 IU/day (which may be adjusted during the stimulation period), until the desired level of follicle production is reached, for a total stimulation period (treatment period) of from about 1 to about 20 days, typically for a total stimulation period of from 8 to 12 days, more specifically typically about 9-11 days, including about 10 days.

The treatment may comprise a further step of administering a GnRH antagonist starting once the lead follicle reaches 14 mm in diameter and/or on the 5$^{th}$ or 6$^{th}$ or 7$^{th}$ day of stimulation (e.g., stimulation day 6), and continued through the remainder of the period of HP-hMG administration.

The treatment of infertility as described herein is associated with a higher probability of live birth, particularly as compared to a comparable method of treatment using CHO cell-derived recombinant follicle stimulating hormone (rFSH) (e.g., GONAL-F, EMD Serono) as the gonadotropin.

The treatment may further comprise triggering final follicular maturation, as described above. Thus, the treatment may comprise administering hCG (e.g. recombinant hCG) or a GnRH agonist to trigger final follicular maturation. As discussed above, when a GnRH agonist is used to trigger final follicular maturation, a small amount of hCG also may be used.

The treatment may further comprise retrieving (e.g. harvesting) oocyte(s); fertilizing (e.g. inseminating) the oocytes (s); and allowing the fertilized oocytes to develop to the blastocyst stage. The fertilization (e.g. insemination) may be in vitro fertilization, optionally intra-cytoplasmic sperm injection (ICSI).

The treatment may be a fresh transfer method comprising retrieving oocyte(s), fertilizing the oocyte(s), allowing the fertilized oocyte(s) to develop to the blastocyst stage, retrieving blastocyst(s), optionally selecting a blastocyst(s) based on assessment of quality/morphology, and implanting a fresh blastocyst (optionally selected based on, e.g., assessment of quality/morphology) in a uterus. The treatment may be a single blastocyst transfer protocol, wherein a single blastocyst is selected for fresh transfer. Optionally, remaining blastocysts can be frozen by methods known in the art for future transfer.

The method may be a frozen transfer method comprising retrieving oocyte(s), fertilizing the oocyte(s), allowing the fertilized oocyte(s) to develop to the blastocyst stage, optionally assessing chromosomal quality of the blastocyst(s), freezing one or more or all blastocyst(s), and implanting a thawed-frozen blastocyst (e.g., a euploid blastocyst selected based on chromosomal assessment) in a uterus. For frozen and "freeze all" methods, selected blastocysts are frozen by methods known in the art for future implantation/transfer.

The method may involve freezing unfertilized oocytes. Thus, the methods may comprise retrieving oocyte(s), freezing one or more or all retrieved oocytes, subsequently thawing one or more frozen oocytes, fertilizing the oocyte(s), allowing the fertilized oocyte(s) to develop to the blastocyst stage, optionally selecting blastocyst(s) based on assessment of quality/morphology, and implanting a blastocyst (optionally selected based on, e.g., visual assessment of quality/morphology) in a uterus. Alternatively, the methods may comprise retrieving oocyte(s), freezing one or more or all retrieved oocytes, subsequently thawing one or more frozen oocytes, fertilizing the oocyte(s), allowing the fertilized oocyte(s) to develop to the blastocyst stage, conducting chromosomal assessment of blastocyst(s), freezing blastocyst(s), and implanting a thawed-frozen blastocyst (e.g., a euploid blastocyst selected based on chromosomal assessment) in a uterus.

In an example, the treatment comprises administering (to the patient) a dose of 150 IU HP-hMG per day from day 1 of treatment, at day 6 of treatment determining whether the patient's serum level of hCG is ≥1.5 mIU/mL, and, optionally, maintaining or increasing the daily dose of HP-hMG (e.g., by an increments of 75 IU/day) based on whether the patient's serum level of hCG is ≥1.5 mIU/mL, such as increasing the daily dose of HP-hMG by 75 IU/day if the patient's serum level of hCG is <1.5 mIU/mL.

According to the present invention there also is provided a composition (e.g., a pharmaceutical composition) comprising HP-hMG for use in the treatment of infertility in a patient (e.g., a woman) predicted to have a high ovarian response to controlled ovarian stimulation to increase the probability of live birth following fresh or frozen embryo transfer, wherein the treatment comprises selecting a patient identified as predicted to have a high ovarian response to controlled ovarian stimulation; conducting controlled ovarian stimulation by administering a daily dose of HP-hMG to the selected patient from day one of treatment (e.g., from day 2 or day 3 of the patients menstrual cycle); at a mid-follicular stage of controlled ovarian stimulation, determining whether the patient's serum level of hCG is at a target mid-follicular threshold level; and, optionally, maintaining or increasing the daily dose of HP-hMG (e.g., by an increments of 75 IU/day) based on whether the patient's serum level of hCG is at or below the target mid-follicular threshold level. The target mid-follicular threshold level of serum hCG may be from 1.3 to 1.7 mIU/mL, and more preferably is 1.5 mIU/mL.

The patient may have a serum anti-Müllerian hormone (AMH) level≥35.7±0.5 pmol/L (≥5.0±0.2 ng/ml) prior to treatment/stimulation. The treatment may comprise a further step of identifying a patient having a serum anti-Müllerian hormone (AMH) level≥35.7±0.5 pmol/L (≥5.0±0.2 ng/ml), such as when measured using a Beckmann-Coulter Gen 2 assay as described in Arce et al., *Fertility and Sterility* 99: 1644-53 (2013), or an equivalent AMH level assessed by a different method, prior to treatment/stimulation.

In examples of the invention, the patient is not an anovulatory patient.

The composition may comprise 75 to 450 IU HP-hMG, such as MENOPUR®. The treatment of infertility may comprise administering (to the patient) a dose of 75 to 450 IU HP-hMG per day, including 75 IU/day, 150 IU/day, 225 IU/day, 300 IU/day, 375 IU/day or 450 IU/day (which may be adjusted during the stimulation period), until the desired level of follicle production is reached, for a total stimulation period (treatment period) of from about 1 to about 20 days, typically for a total stimulation period of from 8 to 12 days, more specifically typically about 9-11 days, including about 10 days.

The treatment may comprise a further step of administering a GnRH antagonist starting once the lead follicle reaches 14 mm in diameter and/or on the 5th or 6th or 7th day of stimulation (e.g., stimulation day 6), and continued through the remainder of the period of HP-hMG administration.

The treatment of infertility as described herein is associated with a higher probability of live birth, particularly as compared to a comparable method of treatment using CHO cell-derived recombinant follicle stimulating hormone (rFSH) (e.g., GONAL-F, EMD Serono) as the gonadotropin.

The treatment may further comprise triggering final follicular maturation, as described above. Thus, the treatment may comprise administering hCG (e.g. recombinant hCG) or a GnRH agonist to trigger final follicular maturation. As discussed above, when a GnRH agonist is used to trigger final follicular maturation, a small amount of hCG also may be used.

The treatment may further comprise retrieving (e.g. harvesting) oocyte(s); fertilizing (e.g. inseminating) the oocytes (s); and allowing the fertilized oocytes to develop to the blastocyst stage. The fertilization (e.g. insemination) may be in vitro fertilization, optionally intra-cytoplasmic sperm injection (ICSI).

The treatment may be a fresh transfer method comprising retrieving oocyte(s), fertilizing the oocyte(s), allowing the fertilized oocyte(s) to develop to the blastocyst stage, retrieving blastocyst(s), optionally selecting a blastocyst(s) based on assessment of quality/morphology, and implanting a fresh blastocyst (optionally selected based on, e.g., assessment of quality/morphology) in a uterus. The treatment may be a single blastocyst transfer protocol, wherein a single blastocyst is selected for fresh transfer. Optionally, remaining blastocysts can be frozen by methods known in the art for future transfer.

The method may be a frozen transfer method comprising retrieving oocyte(s), fertilizing the oocyte(s), allowing the fertilized oocyte(s) to develop to the blastocyst stage, optionally assessing chromosomal quality of the blastocyst(s), freezing one or more or all blastocyst(s), and implanting a thawed-frozen blastocyst (e.g., a euploid blastocyst selected based on chromosomal assessment) in a uterus. For frozen and "freeze all" methods, selected blastocysts are frozen by methods known in the art for future implantation/transfer.

The method may involve freezing unfertilized oocytes. Thus, the methods may comprise retrieving oocyte(s), freezing one or more or all retrieved oocytes, subsequently thawing one or more frozen oocytes, fertilizing the oocyte(s), allowing the fertilized oocyte(s) to develop to the blastocyst stage, optionally selecting blastocyst(s) based on assessment of quality/morphology, and implanting a blastocyst (optionally selected based on, e.g., visual assessment of quality/morphology) in a uterus. Alternatively, the methods may comprise retrieving oocyte(s), freezing one or more or all retrieved oocytes, subsequently thawing one or more frozen oocytes, fertilizing the oocyte(s), allowing the fertilized oocyte(s) to develop to the blastocyst stage, conducting chromosomal assessment of blastocyst(s), freezing blastocyst(s), and implanting a thawed-frozen blastocyst (e.g., a euploid blastocyst selected based on chromosomal assessment) in a uterus.

In an example, the treatment comprises administering (to the patient) a dose of 150 IU HP-hMG per day from day 1 of treatment, at day 6 of treatment determining whether the patient's serum level of hCG is ≥1.5 mIU/mL, and, optionally, maintaining or increasing the daily dose of HP-hMG (e.g., by an increments of 75 IU/day) based on whether the patient's serum level of hCG is ≥1.5 mIU/mL, such as increasing the daily dose of HP-hMG by 75 IU/day if the patient's serum level of hCG is <1.5 mIU/mL.

In alternative embodiments, the treatment methods described herein comprise administering hCG when the patient's serum hCG level is below a target level, e.g., supplementing the HP-hMG with hCG. Suitable hCG products are commercially available, including NOVAREL® (Ferring Pharmaceuticals, Inc.), PREGNYL® (Merck), and OVIDREL® (EMD Serono) When used for this purpose, hCG is administered at a dose selected to achieve the target last day threshold serum hCG level by the last day of stimulation, such as at a dose of 5-60 IU/day (or an equivalent amount of OVIDREL®, which is dosed in micrograms, e.g., 0.20-2.3 µg/day).

In accordance with such embodiments, an assisted reproductive technology treatment method as described herein may comprise conducting controlled ovarian stimulation in an identified predicted high responder by administering a daily dose of HP-hMG effective to stimulate follicle development, and, at a mid-follicular stage of the stimulation period (such as, for example, on stimulation day 5 or 6 or 7), determining whether the patient's serum hCG level is at a target mid-follicular threshold level (such as ≥1.5 mIU/mL) and, optionally, administering hCG (e.g., at a dose of 5-60 IU/day) based on whether the patient's serum hCG level is at the target mid-follicular threshold level. The hCG supplementation may continue throughout the remainder of the stimulation period.

In accordance with these embodiments, hCG supplementation may be conducted in addition to or as an alternative to increasing the daily dose of HP-hMG. Thus, for example, if the patient's serum hCG level is not at the target mid-follicular threshold level, hCG may be administered and, optionally, the daily dose of HP-hMG may be increased.

In some embodiments, the patient's serum hCG level may be determined again (e.g., 1-3 days after the first determination) and, the method may further comprise optionally (i) maintaining or increasing the daily dose of HP-hMG and/or (ii) maintaining or increasing the daily dose of hCG, based on whether the patient's serum hCG level is at a target level, wherein the target level for the subsequent determination is selected to achieve the target last day threshold serum hCG by the last day of stimulation (such as ≥1.5, or ≥1.6, or ≥1.7 mIU/mL for a target last day threshold of 1.8 mIU/mL).

In variations of the HP-hMG embodiments discussed above, the daily dose of HP-hMG may be increased after a first determination that the patient's serum hCG level is not at a target mid-follicular threshold level (such as ≥1.5 mIU/mL), and hCG supplementation may be commenced after a subsequent determination that the patient's serum hCG level is not at a target threshold level, or vice versa.

Thus, according to the present invention there is provided a composition comprising HP-hMG for use in the treatment of infertility in a patient predicted to have a high ovarian response to controlled ovarian stimulation, wherein the treatment comprises selecting a patient identified as predicted to have a high ovarian response to controlled ovarian stimulation; conducting controlled ovarian stimulation by administering a daily dose of HP-hMG to the selected patient from day one of treatment (e.g., from 75-450 IU/day, preferably from 75-225 IU/day, more preferably 150 or 225 IU/day, most preferably 150 IU/day); at a mid-follicular stage of controlled ovarian stimulation (e.g., at stimulation day 5 or 6 or 7), determining whether the patient's serum level of hCG is at a target mid-follicular threshold level (e.g., ≥1.5 mIU/mL); and, optionally, administering hCG to the patient based on whether the patient's serum level of hCG is at or below the target mid-follicular threshold level. The method may comprise administering hCG at a daily dose of 5-60 IU/day when the patient's serum level of hCG is below the target mid-follicular threshold level.

In further alternative embodiments, the treatment methods described herein comprise using FSH (such as rFSH) as the gonadotropin for controlled ovarian stimulation, such as in accordance with protocols known in the art. As used herein "rFSH" includes recombinant human FSH products approved for use for controlled ovarian stimulation, such as follitropin alfa (GONAL-F, Merck Serono/EMD Serono) and follitropin beta (PUREGON® and FOLLISTIM®, MSD/Schering-Plough), which are expressed in a Chinese hamster ovary (CHO) cell line, as well as follitropin delta (REKOVELLE®, Ferring) which is expressed in a human cell line. For example, CHO cell-derived rFSH products may be administered at a dose of from 75-450 IU/day, with a typical starting dose of from 75-225 IU/day, such as 150 IU/day or 225 IU/day, typically 150 IU/day. Human cell-derived rFSH products, such as REKOVELLE®, may be dosed on a microgram basis, at a daily dose of from 6-24 μg, with a typical starting dose of from 12-15 μg/day.

In accordance with such embodiments, hCG supplementation is commenced at a mid-follicular stage, in order to achieve a target last day serum hCG level (e.g., ≥1.8 mIU/mL) by the last day of controlled ovarian stimulation. When used for this purpose, hCG (e.g., NOVAREL®, Ferring Pharmaceuticals, Inc.; PREGNYL®, Merck; or OVIDREL®, EMD Serono) is administered at a dose selected to achieve the target last day threshold serum hCG level by the last day of stimulation, such as at a dose of 5-60 IU/day (or an equivalent amount of OVIDREL®, which is dosed in micrograms, e.g., 0.20-2.3 μg/day).

In accordance with such embodiments, an assisted reproductive technology treatment method as described herein may comprise conducting controlled ovarian stimulation in an identified predicted high responder by administering a daily dose of rFSH effective to stimulate follicle development, and, at a mid-follicular stage of the stimulation period (such as, for example, on stimulation day 5 or 6 or 7), administering hCG (e.g., at a dose of 5-60 IU/day). The hCG supplementation may continue throughout the remainder of the stimulation period. In some embodiments, the patient's serum hCG level may be determined 1-3 days after commencement of hCG supplementation, and the method may further comprise optionally maintaining or increasing the daily dose of hCG, based on whether the patient's serum hCG level is at a target level, wherein the target level for the subsequent determination is selected to achieve the target last day threshold serum hCG by the last day of stimulation (such as ≥1.5, or ≥1.6, or ≥1.7 mIU/mL for a target last day threshold of ≥1.8 mIU/mL).

Thus, according to the present invention in a further aspect there is provided a composition comprising rFSH for use in the treatment of infertility in a patient predicted to have a high ovarian response to controlled ovarian stimulation, wherein the treatment comprises selecting a patient identified as predicted to have a high ovarian response to controlled ovarian stimulation; conducting controlled ovarian stimulation by administering a daily dose of rFSH effective to stimulate follicle development to the selected patient from day one of treatment (e.g., from 75-450 IU/day, preferably from 75-225 IU/day, more preferably 150 or 225 IU/day, most preferably 150 IU/day for CHO cell-derived rFSH products, or from 6-24 μg/day, preferably from 12-15 μg/day, for human cell line-derived rFSH products); and, starting from a mid-follicular stage of controlled ovarian stimulation (e.g. starting on stimulation day 5 or 6 or 7), administering hCG to the patient at a daily dose of 5-60 IU/day.

In a related aspect there is provided a composition comprising hCG for use in the treatment of infertility in a patient predicted to have a high ovarian response to controlled ovarian stimulation, wherein the treatment comprises selecting a patient identified as predicted to have a high ovarian response to controlled ovarian stimulation; conducting controlled ovarian stimulation by administering a daily dose of rFSH effective to stimulate follicle development to the selected patient from day one of treatment (e.g., from 75-450 IU/day, preferably from 75-225 IU/day, more preferably 150 or 225 IU/day, most preferably 150 IU/day for CHO cell-derived rFSH products, or from 6-24 μg/day, preferably from 12-15 μg/day, for human cell line-derived rFSH products); and, starting from a mid-follicular stage of controlled ovarian stimulation (e.g. starting on stimulation day 5 or 6 or 7), administering hCG to the patient at a daily dose of 5-60 IU/day.

In a related aspect there is provided a product comprising rFSH and hCG (e.g. in separate containers) for use in the treatment of infertility in a patient predicted to have a high ovarian response to controlled ovarian stimulation, wherein the treatment comprises selecting a patient identified as predicted to have a high ovarian response to controlled ovarian stimulation; conducting controlled ovarian stimulation by administering a daily dose of rFSH effective to stimulate follicle development to the selected patient from day one of treatment (e.g., from 75-450 IU/day, preferably from 75-225 IU/day, more preferably 150 or 225 IU/day, most preferably 150 IU/day for CHO cell-derived rFSH products, or from 6-24 μg/day, preferably from 12-15 μg/day, for human cell line-derived rFSH products); and, starting from a mid-follicular stage of controlled ovarian stimulation (e.g. starting on stimulation day 5 or 6 or 7), administering hCG to the patient at a daily dose of 5-60 IU/day.

Further aspects of the methods described herein are illustrated in the following examples, which are not limiting in any respect.

EXAMPLES

Example 1

MEGASET HR Clinical Trial and Retrospective Analysis

The following describes a retrospective analysis of data collected in a multicenter, randomized, assessor-blind, controlled non-inferiority trial in 620 women, 21-35 years, with BMI 18-30 kg/m² and serum anti-Müllerian hormone (AMH)≥35.7 pmol/L undergoing intracytoplasmic sperm injection and single blastocyst transfer (fresh transfer). The trial was titled "MENOPUR® in a Gonadotropin-Releasing Hormone (GnRH) Antagonist Cycle With Single-Blastocyst Transfer in a High Responder Subject Population (MEGASET HR)" (ClinicalTrials.gov identifier NCT02554279). Further details can be found at clinicaltrials.gov/ct2/show/ record/NCT02554279 and in Witz et al., *Fertility and Sterility*, in press (published on line Mar. 29, 2020).

1. Study Population

The main inclusion criteria were for females aged 21 to 35 years with regular ovulatory menstrual cycles of 21 to 45 days, with a Body Mass Index (BMI) between 18 and 30 kg/m² who desire pregnancy. The patients/subjects were predicted-high responders, which was defined as subjects who have a serum anti-Müllerian hormone (AMH)≥5 ng/mL (35.71 pmol/L) at screening. The subjects had a documented history of infertility (e.g., unable to conceive for at least 12 months or for at least 6 months if receiving donor sperm) with a menstrual cycle day 2 or day 3 serum FSH level between 1 and 12 IU/L (inclusive).

The exclusion criteria were known stage III-IV endometriosis; history of recurrent miscarriage not followed by a live birth (with recurrent defined as two or more consecutive miscarriages); and previous in vitro fertilization (IVF) or assisted reproductive technology (ART) failure due to a poor response to gonadotropins (with poor response defined as development of ≤2 mature follicles or history of 2 previous failed cycle cancellations prior to oocytes retrieval due to poor response). Anovulatory women also were excluded.

2. Study Protocol

This was a multicenter, randomized, assessor-blind phase IV clinical trial comparing HP-hMG and rFSH in a GnRH antagonist cycle with compulsory single-blastocyst transfer (fresh transfer) in a high responder subject population in the United States. The aim of this study was to demonstrate that HP-hMG is at least non-inferior to rFSH with respect to ongoing pregnancy rate (OPR) in potential high-responders undergoing IVF/ICSI treatment.

Subjects were classified as potential high ovarian responders based on a serum level of AMH≥5.0 ng/ml (e.g. ≥35.7 pmol/L) by the Beckmann-Coulter Gen 2 assay as described in Arce et al., *Fertility and Sterility* 99: 1644-53 (2013), using a single reference laboratory (ReproSource, Inc., Woburn, MA) utilizing materials and reagents from the Beckman Coulter-DSL assay (Chaska, MN).

Subjects were randomized 1:1 to undergo COS with either a 150 IU dose of HP-hMG (N=311; MENOPUR®, Ferring Pharmaceuticals, Inc.) or rFSH (N=309; GONAL-F, E Serono) as the gonadotropin in a GnRH antagonist cycle. Treatment was initiated on day 2 or 3 of the menstrual cycle at a dose of 150 IU HP-hMG or rFSH for the first 5 days. From Stimulation day 6 onward, dosing could be adjusted every day as needed by 75 IU per adjustment, based on follicular response assessed by TVUS. However, the maximum gonadotropin dose was 300 IU/day. Gonadotropin dosing could continue for a maximum of 20 days and coasting was prohibited.

When the lead follicle was >14 mm in diameter, a GnRH antagonist (ganirelix acetate) was initiated at a daily dose of 0.25 mg and continued throughout the gonadotropin treatment period.

A single injection of 250 µg hCG (choriogonadotropin alfa) was administered to induce final follicular maturation as soon as 3 follicles of ≥17 mm diameter were observed on TVUS.

However, if a subject had excessive ovarian response (>30 follicles of ≥12 mm each and/or estradiol (E2) levels≥5,000 pg/mL), a GnRH agonist (4 mg leuprolide acetate) was administered≥12 hours after the last GnRH antagonist dose, fresh transfer was canceled, all blastocysts were biopsied; and viable blastocysts were frozen for use in a subsequent transfer cycle in order to decrease risk of OHSS.

Oocyte retrieval took place roughly 36 hours after hCG or GnRH agonist administration. Oocytes were inseminated using partner sperm by ICSI 4±1 hours after retrieval. Oocyte, embryo and blastocyst quality were assessed. On Day 5 following ICSI, a single blastocyst of the best quality by morphology (Gardner and Schoolcraft scale) was transferred (fresh transfer); all remaining blastocysts were frozen using the vitrification method.

The day after oocyte retrieval, vaginal progesterone inserts (100 mg twice a day—ENDOMETRIN®; Ferring) were initiated for luteal phase support and this continued until the day of the β-hCG test (10 to 15 days after blastocyst/embryo transfer). Luteal support could be continued until ongoing pregnancy was confirmed.

Biochemical pregnancy was confirmed by a positive β-hCG test approximately 2 weeks after blastocyst transfer. Clinical pregnancy was confirmed by TVUS indicating at least one intrauterine gestational sac with fetal heart beat at 5 to 6 weeks gestation. Ongoing pregnancy was confirmed by at least one intrauterine viable fetus at 10 to 11 weeks gestation.

For subjects with no ongoing pregnancy in the fresh cycle, single frozen blastocyst transfers could be initiated within 6 months of the subject's randomization in the trial. PGS results could be used to select euploid blastocysts for frozen transfer. Frozen-thawed embryo transfer cycle data was collected, including blastocyst transfer information, β-hCG test, clinical pregnancy, ongoing pregnancy, pregnancy loss rate and live birth.

Post-trial follow-up included collection of delivery information (live birth and neonatal health), which was collected for all subjects with an ongoing pregnancy in the fresh cycle or the 1-year post-randomization frozen-thawed embryo replacement cycles. Live birth rate after the fresh cycle and cumulative live birth rate after fresh and 6-month post-randomization frozen-thawed embryo replacement cycles were evaluated as part of the post-trial follow-up.

The HP-hMG used was MENOPUR® (provided by Ferring Pharmaceuticals, Inc.), provided as a vial containing dry HP-hMG (75 IU HP-hMG, providing 75 IU FSH activity and 75 IU LH activity, including LH activity provided by hCG) and vials containing solvent for reconstitution. After reconstitution, each vial contains 75 IU of FSH activity and 75 IU of LH activity, including LH activity provided by hCG.

The FSH used was recombinant FSH (GONAL-F, EMD Serono), provided as solution for injection.

The other drugs used were:

Ganirelix Acetate Injection, manufactured by Merck, provided as a pre-filled syringe (0.5 mL) delivering 0.25 mg ganirelix. Once the lead follicle measures≥14 mm and/or serum E2 levels are ≥300 pg/mL, ganirelix acetate was initiated at a daily dose of 0.25 mg and continued throughout the gonadotropin treatment period.

OVIDREL® (choriogonadotropin alfa), manufactured by EMD Serono, provided as a pre-filled syringe (0.5 mL) delivering 250 µg choriogonadotropin alfa, administered as a single injection as soon as 3 follicles of ≥17 mm diameter were observed on TVUS.

ENDOMETRIN® (progesterone), manufactured by Ferring, provided as inserts to be administered vaginally 2 times daily, each delivering 100 mg (200 mg/day).

The primary end point was ongoing pregnancy rate, with ongoing pregnancy defined as presence of at least one intrauterine pregnancy with a viable fetus with a detectable fetal heartbeat at 10-11 weeks gestation. Secondary endpoints included:

biochemical pregnancy rate (positive β-hCG test)

clinical pregnancy rate (transvaginal ultrasonography showing at least one intrauterine gestational sac with fetal heart beat at 5-6 weeks gestation)

early pregnancy loss (defined as 2 positive β-hCG tests but no ongoing pregnancy at 10-11 weeks gestation in the fresh cycle.)

live birth rate follicular development as assessed by TVUS, follicle level (total number of follicles, number of follicles≤9 mm, 10-11 mm, 12-14 mm, 15-16 mm, and ≥17 mm) and subject level (largest follicle size, average follicle size, average size of 3 largest follicles, and average number of follicles≥17 mm, ≥15 mm, and ≥12 mm)

endocrine profile (serum estradiol [E2], progesterone [P4], hCG, LH)

oocytes retrieved, fertilization rate, and embryo quality

3. Serum Assays

Blood samples were taken prior to and throughout the stimulation period, including prior to start of stimulation, on stimulation day 6, and on the last day of stimulation. Serum was analyzed using ELISA for AMH (Beckman Coulter Gen 2), FSH, LH, and hCG, using two dimensional high performance liquid chromatography with tandem mass spectrometry for estradiol and using liquid chromatography with tandem mass spectrometry for progesterone and testosterone. The lower detection limits were as follows: FSH 0.017 mIU/mL; LH 0.005 mIU/mL; βhCG 0.5 mIU/mL; estradiol 1.0 pgl/mL, progesterone 10 ng/dL, and testosterone 2.5 ng/dL.

4. Results and Retrospective Analysis

The non-inferiority objective for the primary endpoint of ongoing pregnancy was met. HP-hMG was associated with numerically higher ongoing pregnancy rates vs rFSH (35.5% vs 30.7%, P>0.05). The average number of oocytes per patient (±SD) in the rFSH arm (22.2±11.54) was higher than in the hMG arm (15.1±10.12), a difference in ovarian response that was accompanied by statistically significant increases in rates of OHSS (21.4% vs 9.7%; p<0.05).

For the present retrospective analysis, live birth outcomes resulting from all fresh transfers and any frozen transfers occurring within 6 months of randomization were collected. Logistic regression was performed to separately identify relationships between each factor (per visit, as appropriate) and the live birth rate. Interaction effects of the factors with the treatment group (HP-hMG, rFSH) were investigated. Results were reported as odds ratio (OR) and 95% confidence intervals (CI) with corresponding p-values.

The retrospective analysis showed that serum hCG on the last day of stimulation in HP-hMG treated subjects had a significant effect on the probability of live birth, with an odds ratio of 1.38 (CI: 1.00, 1.89) (p-value: 0.048). For every 1 mIU/mL increase in hCG, the odds of live birth increased by 38%. Serum hCG on day 6 of stimulation was not a statistically significant predictor of live birth in the HP-hMG group (p=0.73). hCG could not be detected in the serum of rFSH treated subjects.

The retrospective analysis also showed a significant serum FSH interaction by treatment group on day 6. For every 1 IU/mL increase in serum FSH, the odds ratio of live birth was reduced by 13% in rFSH-treated subjects as compared to HP-hMG treated subjects, with an odds ratio of 0.87 (CI: 0.77, 0.98) (p-value: 0.020). This difference between treatment groups is seen even though the HP-hMG includes FSH activity, indicating that the effect seen in rFSH-treated subjects may be due to FSH that is not counterbalanced by hCG.

No other significant relationships to live birth were found in the time points/parameters evaluated.

While not wanting to be bound by theory, the present analyses suggest that hCG derived from HP-hMG (e.g., provided by HP-hMG) contributes positively to the likelihood of live birth when used in controlled ovarian stimulation of predicted-high responders. The cause of this relationship is not clear. However, fewer fresh and frozen transfers were required to reach similar cumulative live birth outcomes in the HP-hMG-treated group as compared to the rFSH-treated group.

Example 2

An exemplary infertility treatment method for predicted-high responders is outlined below. The infertility treatment targeting a serum hCG threshold level on the last day of COS through HP-hMG dosing is associated with a higher probability of live birth.

Typically, a medical practitioner (e.g., a physician) will oversee the treatment of infertility. The patient will be, or will have been, diagnosed as a predicted-high responder, such as by a serum AMH test, for example, based on having a serum level of AMH≥35.7±0.5 pmol/L (≥5.0±0.2 ng/ml) by the Beckmann-Coulter Gen 2 assay as described in Arce et al., *Fertility and Sterility* 99: 1644-53 (2013), or an equivalent serum AMH level determined by a different method.

A patient predicted as being a high responder (e.g., having a serum level of AMH≥35.7±0.5 pmol/L or ≥5.0±0.2 ng/ml prior to treatment) is selected and administered HP-hMG (for example MENOPUR®, available from Ferring Pharmaceuticals, Inc.). As discussed above, MENOPUR® is believed to be particularly advantageous in this application because it includes hCG-driven LH activity.

Controlled ovarian stimulation is begun ("stimulation day 1") on day 2 or 3 of the patient's menstrual cycle. The treatment comprises administering a daily dose of MENOPUR®, such as 150 IU/day, by injection from day 1 (stimulation day 1) to at least day 5 (stimulation day 5) of treatment. As discussed below, the dose may be adjusted (e.g., depending on the patient's ovarian response and/or serum hCG) up or down (e.g., in increments of 75 IU hMG) to a maximum daily dose of 450 IU hMG or minimum daily dose of 75 IU hMG. The treatment may continue for up to 20 days (up to and including stimulation day 20), but typically is for 8-12 days, including about 10 days.

When the lead follicle is >14 mm in diameter, as assessed by TVUS, a GnRH antagonist (ganirelix acetate) may be initiated at a daily dose of 0.25 mg and continued throughout the gonadotropin stimulation treatment period.

During the stimulation period, at a mid-follicular stage (such as, for example, on stimulation day 6), the patient's serum hCG level is determined (e.g., by ELISA with a limit of detection of at least 0.5 mIU/mL), and it is determined whether the patient's serum hCG level is at a mid-follicular target level. For this determination, blood typically is collected at least 8 hours after the previous gonadotrophin dose. If the serum hCG level is below a target mid-follicular threshold level (such as below 1.5 mIU/mL), the daily dose of HP-hMG is increased (e.g., by 75 IU/day). The increased daily dose is continued throughout the remainder of the stimulation period (e.g., as long as continuing the increased dose is not contraindicated by other safety factors, such as high ovarian response), with the aim of achieving the target threshold level of hCG at the end of stimulation (e.g., ≥1.8 mIU/mL by the time 3 follicles of ≥17 mm diameter are observed on TVUS). The method may optionally comprise determining serum hCG on the last day of stimulation, although by that time it is too late to intervene if the level is lower than the desired target threshold level.

Final follicular maturation is triggered with hCG or a GnRH agonist. A single injection of 250 µg hCG (choriogonadotropin alfa) may be administered to induce final follicular maturation as soon as 3 follicles of ≥17 mm diameter are observed on TVUS. Alternatively, a GnRH agonist may be used to trigger final follicular maturation, such as in the event of excessive response to COS, such as in a patient who, following COS treatment, has >30 follicles of ≥12 mm diameter or serum estradiol (E2) levels>5,000 pg/ml. When a GnRH agonist is used, it may be, e.g., leuprolide acetate, e.g., LUPRON®, at a dose of, e.g., 1-4 mg.

The method further comprises oocyte retrieval (generally roughly 36 hours after triggering final follicular maturation), fertilization, and subsequent procedures including retrieving blastocyst(s), and implanting a fresh blastocyst in a uterus, in accordance with the protocols described above and variations thereof that are known in the art.

There have been disclosed hereinbefore the compositions, compositions for use, uses and methods defined by the following numbered paragraphs:

1. A composition comprising HP-hMG for use in the treatment of infertility in a patient predicted to have a high ovarian response to controlled ovarian stimulation, wherein the treatment comprises:

selecting a patient identified as predicted to have a high ovarian response to controlled ovarian stimulation;

conducting controlled ovarian stimulation by administering a daily dose of HP-hMG to the patient from day one of treatment (e.g., from 75-450 IU/day, preferably from 75-225 IU/day, more preferably 150 or 225 IU/day, most preferably 150 IU/day);

at a mid-follicular stage of controlled ovarian stimulation (e.g., at stimulation day 5 or 6 or 7), determining if the patient's serum level of hCG is at a target mid-follicular threshold level (e.g., >1.5 mIU/mL); and triggering final follicular maturation when the level of hCG in the patient's serum is at, or above, a specified threshold level of serum hCG at final follicular maturation which leads to an increased probability of live birth.

2. A composition comprising HP-hMG for use in the treatment of infertility in a patient predicted to have a high ovarian response to controlled ovarian stimulation to increase the probability of live birth following fresh or frozen embryo transfer, wherein the treatment comprises:

selecting a patient identified as predicted to have a high ovarian response to controlled ovarian stimulation;

conducting controlled ovarian stimulation by administering a daily dose of HP-hMG to the patient from day one of treatment (e.g., from 75-450 IU/day, preferably from 75-225 IU/day, more preferably 150 or 225 IU/day, most preferably 150 IU/day);

at a mid-follicular stage of controlled ovarian stimulation (e.g., at stimulation day 5 or 6 or 7), determining if the patient's serum level of hCG is at a target mid-follicular threshold level (e.g., ≥1.5 mIU/mL); and triggering final follicular maturation when the level of hCG in the patient's serum is at, or above, a specified threshold level of serum hCG at final follicular maturation which leads to an increased probability of live birth.

3. A composition for use according to any one of paragraphs 1-2, wherein the specified threshold level of serum hCG at final follicular maturation which leads to an increased probability of live birth is selected from 1.5-2.0 mIU/mL, more preferably 1.8 mIU/mL.

4. A composition comprising HP-hMG for use in the treatment of infertility in a patient predicted to have a high ovarian response to controlled ovarian stimulation, wherein the treatment comprises:

selecting a patient identified as predicted to have a high ovarian response to controlled ovarian stimulation;

conducting controlled ovarian stimulation by administering a daily dose of HP-hMG to the selected patient from day one of treatment (e.g., from 75-225 IU/day, preferably from 75-225 IU/day, more preferably 150 or 225 IU/day, most preferably 150 IU/day);

at a mid-follicular stage of controlled ovarian stimulation (e.g., at stimulation day 5 or 6 or 7), determining whether the patient's serum level of hCG is at a target mid-follicular threshold level (e.g., ≥1.5 mIU/mL); and, optionally, maintaining or increasing the daily dose of HP-hMG (e.g., by 75 IU/day) based on whether the patient's serum level of hCG is at or below the target mid-follicular threshold level.

5. A composition comprising HP-hMG for use in the treatment of infertility in a patient predicted to have a high ovarian response to controlled ovarian stimulation to increase the probability of live birth following fresh or frozen embryo transfer, wherein the treatment comprises:

selecting a patient identified as predicted to have a high ovarian response to controlled ovarian stimulation;

conducting controlled ovarian stimulation by administering a daily dose of HP-hMG to the selected patient from day one of treatment (e.g., from 75-450 IU/day, preferably from 75-225 IU/day, more preferably 150 or 225 IU/day, most preferably 150 IU/day);

at a mid-follicular stage of controlled ovarian stimulation (e.g., at stimulation day 5 or 6 or 7), determining whether the patient's serum level of hCG is at a target mid-follicular threshold level (e.g., ≥1.5 mIU/mL); and, optionally, maintaining or increasing the daily dose of HP-hMG (e.g., by 75 IU/day) based on whether the patient's serum level of hCG is at or below the target mid-follicular threshold level.

6. A composition for use according to any preceding paragraph, wherein the patient has a serum anti-Müllerian hormone (AMH) level≥35.7±0.5 pmol/L (≥5.0±0.2 ng/ml) prior to treatment/stimulation.

7. A composition for use according to any preceding paragraph, wherein the treatment further comprises, prior to stimulation, identifying the patient as having a serum anti-Müllerian hormone (AMH) level≥35.7±0.5 pmol/L (≥5.0±0.2 ng/ml).

8. A composition for use according to any preceding paragraph, wherein the patient is not anovulatory.

9. A composition for use according to any preceding paragraph, wherein the patient is 21-35 years old and has a BMI of 18-30 kg/m$^2$ at the start of treatment.

10. A composition for use according to any preceding paragraph comprising 75 to 450 IU HP-hMG.

11. A composition for use according to any preceding paragraph, wherein the controlled ovarian stimulation comprises administering HP-hMG at a starting dose of 75 to 225 IU hMG per day, preferably 150 IU/day, e.g. from day 1 to at least day 5 of stimulation.

12. A composition for use according to any preceding paragraph, wherein the treatment of infertility increases the probability of live birth compared to treatment with CHO cell-derived recombinant FSH.

13. A composition for use according to any preceding paragraph, wherein the treatment further comprises triggering final follicular maturation by administering hCG or a GnRH agonist, optionally supplemented with hCG.

14. A composition for use according to any preceding paragraph, wherein the treatment further comprises administering a GnRH antagonist starting on day 6 of stimulation.

15. A composition for use according to any preceding paragraph wherein the treatment further comprises:

retrieving oocyte(s), fertilizing the oocyte(s), allowing the fertilized oocyte(s) to develop to the blastocyst stage, optionally assessing the quality/morphology of the blastocyst(s), and implanting a fresh blastocyst (optionally selected based on, e.g., visual assessment of quality/morphology) in a uterus; or retrieving oocyte(s), fertilizing the oocyte(s), allowing the fertilized oocyte(s) to develop to the blastocyst stage, optionally assessing chromosomal quality of the blastocyst(s), freezing one or more or all blastocyst(s), and implanting a thawed-frozen blastocyst (e.g., a euploid blastocyst selected based on chromosomal assessment) in a uterus; or retrieving oocyte(s), freezing unfertilized oocytes(s), subsequently thawing one or more oocyte(s), fertilizing one or more or all thawed oocyte(s), allowing fertilized oocyte(s) to develop to the blastocyst stage, optionally assessing the quality/morphology of the blastocyst(s), and implanting a blastocyst (optionally selected based on, e.g., visual assessment of quality/ morphology) in a uterus; or retrieving oocyte(s), freezing unfertilized oocytes(s), subsequently thawing one or more frozen oocytes, fertilizing one or more or all thawed oocyte(s), allowing fertilized oocyte(s) to develop to the blastocyst stage, optionally assessing chromosomal quality of the blastocyst(s), freezing one or more or all blastocyst(s), and implanting a thawed-frozen blastocyst (e.g., a euploid blastocyst selected based on chromosomal assessment) in a uterus.

16. A method of treating infertility by controlled ovarian stimulation in a patient predicted to have a high ovarian response to controlled ovarian stimulation, comprising:

selecting a patient identified as predicted to have a high ovarian response to controlled ovarian stimulation;

conducting controlled ovarian stimulation by administering to the selected patient HP-hMG at a starting daily dose of 75 IU to 225 IU;

at a mid-follicular stage of controlled ovarian stimulation, determining if the patient's serum level of hCG is at a target mid-follicular threshold level; and optionally, maintaining or increasing the daily dose of HP-hMG based on whether the patient's serum level of hCG is at or below the target mid-follicular threshold level.

17. The method of paragraph 16, wherein the patient is not anovulatory.

18. The method of paragraph 16, wherein the patient is 21-35 years old and has a BMI of 18-30 kg/m² at the start of treatment.

19. The method of paragraph 16, wherein the method comprises increasing the daily dose of HP-hMG when the patient's serum level of hCG is below the target mid-follicular threshold level.

20. The method of paragraph 16, wherein the method comprises increasing the daily dose of HP-hMG by 75 IU/day when the patient's serum level of hCG is below the target mid-follicular threshold level.

21. The method of paragraph 16, wherein the method comprises maintaining the daily dose of HP-hMG when the patient's serum level of hCG is at the target mid-follicular threshold level.

22. The method of any one of paragraphs 16-21, wherein the target mid-follicular threshold level of serum hCG is >1.5 mIU/mL.

23. The method of any one of paragraphs 16-21, wherein the mid-follicular stage of controlled ovarian stimulation is selected from stimulation day 5, stimulation day 6, and stimulation day 7.

24. The method of any one of paragraphs 16-21, wherein the starting daily dose of HP-hMG is 150 IU/day.

25. The method of any one of paragraphs 16-21, further comprising administering a gonadotropin-releasing hormone antagonist (GnRH antagonist) starting on day 6 of stimulation.

26. The method of any one of paragraphs 16-21, further comprising triggering final follicular maturation by administering human chorionic gonadotropin (hCG) or a gonadotropin-releasing hormone agonist (GnRH agonist), optionally supplemented with hCG.

27. The method of any one of paragraphs 16-21, further comprising:

(a) retrieving oocyte(s), fertilizing the oocyte(s), allowing the fertilized oocyte(s) to develop to the blastocyst stage, optionally assessing the quality/morphology of the blastocyst(s), and implanting a fresh blastocyst (optionally selected based on, e.g., visual assessment of quality/morphology) in a uterus; or (b) retrieving oocyte(s), fertilizing the oocyte(s), allowing the fertilized oocyte(s) to develop to the blastocyst stage, optionally assessing chromosomal quality of the blastocyst(s), freezing one or more or all blastocyst(s), and implanting a thawed-frozen blastocyst (e.g., a euploid blastocyst selected based on chromosomal assessment) in a uterus; or (c) retrieving oocyte(s), freezing unfertilized oocytes (s), subsequently thawing one or more oocyte(s), fertilizing one or more or all thawed oocyte(s), allowing fertilized oocyte(s) to develop to the blastocyst stage, optionally assessing the quality/morphology of the blastocyst(s), and implanting a blastocyst (optionally selected based on, e.g., visual assessment of quality/morphology) in a uterus; or (d) retrieving oocyte(s), freezing unfertilized oocytes (s), subsequently thawing one or more frozen oocytes, fertilizing one or more or all thawed oocyte (s), allowing fertilized oocyte(s) to develop to the blastocyst stage, optionally assessing chromosomal quality of the blastocyst(s), freezing one or more or all blastocyst(s), and implanting a thawed-frozen blastocyst (e.g., a euploid blastocyst selected based on chromosomal assessment) in a uterus.

28. A method of treating infertility by controlled ovarian stimulation in a patient predicted to have a high ovarian response to controlled ovarian stimulation, comprising:

selecting a patient identified as predicted to have a high ovarian response to controlled ovarian stimulation;

conducting controlled ovarian stimulation by administering to the selected patient HP-hMG at a starting daily dose of 75 IU to 225 IU;

at a mid-follicular stage of controlled ovarian stimulation, determining if the patient's serum level of hCG is at a target mid-follicular threshold level; and optionally, administering hCG to the patient based on whether the patient's serum level of hCG is at or below the target mid-follicular threshold level.

29. The method of paragraph 28, wherein the method comprises administering hCG at a daily dose of, or equivalent to, 5-60 IU/day when the patient's serum level of hCG is below the target mid-follicular threshold level.

30. A method of treating infertility by controlled ovarian stimulation in a patient predicted to have a high ovarian response to controlled ovarian stimulation, comprising:

selecting a patient identified as predicted to have a high ovarian response to controlled ovarian stimulation;

conducting controlled ovarian stimulation by administering to the selected patient rFSH at a daily dose effective for controlled ovarian stimulation; and starting at a mid-follicular stage of controlled ovarian stimulation, administering hCG to the patient at a daily dose of, or equivalent to, 5-60 IU/day.

The invention claimed is:

1. A method of treating infertility in a patient having a serum anti-Müllerian hormone (AMH) level≥35.7±0.5 pmol/L (≥5.0±0.2 ng/ml) prior to treatment/stimulation, comprising:

selecting a patient identified as having a serum anti-Müllerian hormone (AMH) level≥35.7±0.5 pmol/L (≥5.0±0.2 ng/ml) prior to treatment/stimulation;

conducting controlled ovarian stimulation by administering a daily dose of 75-450 IU highly purified human menopausal gonadotropin (HP-hMG) to the selected patient from day one of treatment;

at stimulation day 5 or 6 or 7 of controlled ovarian stimulation, determining whether the patient's serum level of human chorionic gonadotrophin (hCG) is at a target mid-follicular threshold level of ≥1.5 mIU/mL; and maintaining or increasing the daily dose of highly purified human menopausal gonadotropin (HP-hMG) based on whether the patient's serum level of human chorionic gonadotrophin (hCG) is at or below the target mid-follicular threshold level.

2. The method according to claim 1, further comprising triggering final follicular maturation when the level of hCG in the patient's serum is at or above a specified threshold level for final follicular maturation of from 1.5-2.0 mIU/mL.

3. The method according to claim 1, further comprising, prior to stimulation, identifying the patient as having a serum anti-Müllerian hormone (AMH) level≥35.7±0.5 pmol/L (≥5.0±0.2 ng/ml).

4. The method according to claim 1, wherein the patient is not anovulatory.

5. The method according to claim 1, wherein the controlled ovarian stimulation comprises administering HP-hMG at a starting dose of 150 IU/day from day 1 to at least day 5 of stimulation.

6. The method according to claim 1, wherein the treatment of infertility increases the probability of live birth compared to treatment with CHO cell-derived recombinant FSH.

7. The method according to claim 1, further comprising triggering final follicular maturation by administering hCG or by administering a GnRH agonist, optionally supplemented with hCG.

8. The method according to claim 1, further comprising administering a GnRH antagonist starting on day 6 of stimulation.

9. The method according to claim 1, further comprising:

retrieving oocyte(s), fertilizing the oocyte(s), allowing the fertilized oocyte(s) to develop to the blastocyst stage, optionally assessing the quality/morphology of the blastocyst(s), and implanting a fresh blastocyst in a uterus; or retrieving oocyte(s), fertilizing the oocyte(s), allowing the fertilized oocyte(s) to develop to the blastocyst stage, optionally assessing chromosomal quality of the blastocyst(s), freezing one or more or all blastocyst(s), and implanting a thawed-frozen blastocyst in a uterus; or retrieving oocyte(s), freezing unfertilized oocytes(s), subsequently thawing one or more oocyte(s), fertilizing one or more or all thawed oocyte(s), allowing fertilized oocyte(s) to develop to the blastocyst stage, optionally assessing the quality/morphology of the blastocyst(s), and implanting a blastocyst in a uterus; or retrieving oocyte(s), freezing unfertilized oocytes(s), subsequently thawing one or more frozen oocytes, fertilizing one or more or all thawed oocyte(s), allowing fertilized oocyte(s) to develop to the blastocyst stage, optionally assessing chromosomal quality of the blastocyst(s), freezing one or more or all blastocyst(s), and implanting a thawed-frozen blastocyst in a uterus.

10. The method according to claim 1, wherein the patient is 21-35 years old and has a BMI of 18-30 kg/m$^2$ at the start of treatment.

11. The method according to claim 1, wherein the method comprises increasing the daily dose of HP-hMG by 75 IU/day when the patient's serum level of hCG is below the target mid-follicular threshold level.

12. The method according to claim 1, wherein the method comprises maintaining the daily dose of HP-hMG when the patient's serum level of hCG is at the target mid-follicular threshold level.

13. A method of treating infertility in a patient having a serum anti-Müllerian hormone (AMH) level≥35.7±0.5 pmol/L (≥5.0±0.2 ng/ml) prior to treatment/stimulation, comprising:

selecting a patient identified as having a serum anti-Müllerian hormone (AMH) level≥35.7±0.5 pmol/L (≥5.0±0.2 ng/ml) prior to treatment/stimulation;

conducting controlled ovarian stimulation by administering a daily dose of 75-450 IU highly purified human menopausal gonadotropin (HP-hMG) to the patient from day one of treatment;

at stimulation day 5 or 6 or 7, determining if the patient's serum level of human chorionic gonadotrophin (hCG) is at a target mid-follicular threshold level of ≥1.5 mIU/mL; and triggering final follicular maturation when the level of human chorionic gonadotrophin (hCG) in the patient's serum is at or above a specified threshold level of serum human chorionic gonadotrophin (hCG) for final follicular maturation selected from 1.5-2.0 mIU/mL which leads to an increased probability of live birth.

14. The method according to claim 13, further comprising, prior to triggering final follicular maturation, increasing the daily dose of HP-hMG by 75 IU/day when the patient's serum level of hCG is below the target mid-follicular threshold level.

15. The method according to claim 13, further comprising, prior to triggering final follicular maturation, maintaining the daily dose of HP-hMG when the patient's serum level of hCG is at the target mid-follicular threshold level.

16. A method of treating infertility in a patient having a serum anti-Müllerian hormone (AMH) level≥35.7±0.5 pmol/L (≥5.0±0.2 ng/ml) prior to treatment/stimulation, comprising:

selecting a patient identified as having a serum anti-Müllerian hormone (AMH) level≥35.7±0.5 pmol/L (>5.0±0.2 ng/ml) prior to treatment/stimulation;

conducting controlled ovarian stimulation by administering a daily dose of 75-450 IU highly purified human menopausal gonadotropin (HP-hMG) to the patient from day one of treatment;

at stimulation day 5 or 6 or 7, determining if the patient's serum level of human chorionic gonadotrophin (hCG) is at a target mid-follicular threshold level of ≥1.5 mIU/mL; and triggering final follicular maturation when the level of human chorionic gonadotrophin (hCG) in the patient's serum is at or above 1.8 mIU/mL which leads to an increased probability of live birth.

17. A method for increasing a probability of live birth following fresh or frozen embryo transfer in the treatment of infertility in a patient having a serum anti-Müllerian hormone (AMH) level≥35.7±0.5 pmol/L (≥5.0±0.2 ng/ml) prior to treatment/stimulation, comprising:

selecting a patient identified as having a serum anti-Müllerian hormone (AMH) level≥35.7±0.5 pmol/L (≥5.0±0.2 ng/ml) prior to treatment/stimulation;

conducting controlled ovarian stimulation by administering a daily dose of 75-450 IU highly purified human menopausal gonadotropin (HP-hMG) to the patient from day one of treatment;

at stimulation day 5 or 6 or 7, determining if the patient's serum level of human chorionic gonadotrophin (hCG) is at a target mid-follicular threshold level of ≥1.5 mIU/mL; and triggering final follicular maturation when the level of human chorionic gonadotrophin (hCG) in the patient's serum is at or above a specified threshold level of serum human chorionic gonadotrophin (hCG) for final follicular maturation selected from 1.5-2.0 mIU/mL which leads to an increased probability of live birth.

18. A method for increasing a probability of live birth following fresh or frozen embryo transfer in the treatment of infertility in a patient having a serum anti-Müllerian hormone (AMH) level≥35.7±0.5 pmol/L (≥5.0±0.2 ng/ml) prior to treatment/stimulation, comprising:

selecting a patient identified as having a serum anti-Müllerian hormone (AMH) level≥35.7±0.5 pmol/L (≥5.0±0.2 ng/ml) prior to treatment/stimulation;

conducting controlled ovarian stimulation by administering a daily dose of 75-450 IU/day highly purified human menopausal gonadotropin (HP-hMG) to the selected patient from day one of treatment;

at stimulation day 5 or 6 or 7, determining whether the patient's serum level of human chorionic gonadotrophin (hCG) is at a target mid-follicular threshold level≥1.5 mIU/mL; and maintaining or increasing the daily dose of highly purified human menopausal gonadotropin (HP-hMG) based on whether the patient's serum level of hCG is at or below the target mid-follicular threshold level.

19. A method of treating infertility in a patient having a serum anti-Müllerian hormone (AMH) level≥35.7±0.5 pmol/L (≥5.0±0.2 ng/ml) prior to treatment/stimulation, comprising:

selecting a patient identified as having a serum anti-Müllerian hormone (AMH) level≥35.7±0.5 pmol/L (≥5.0±0.2 ng/ml) prior to treatment/stimulation;

conducting controlled ovarian stimulation by administering a daily dose of 75-450 IU highly purified human menopausal gonadotropin (HP-hMG) to the selected patient from day one of treatment;

at stimulation day 5 or 6 or 7 of controlled ovarian stimulation, determining whether the patient's serum level of human chorionic gonadotrophin (hCG) is at a target mid-follicular threshold level of ≥1.5 mIU/mL;

maintaining or increasing the daily dose of highly purified human menopausal gonadotropin (HP-hMG) based on whether the patient's serum level of human chorionic gonadotrophin (hCG) is at or below the target mid-follicular threshold level; and triggering final follicular maturation when the level of human chorionic gonadotrophin (hCG) in the patient's serum is at or above 1.8 mIU/mL.

* * * * *